(12) United States Patent
Mougin et al.

(10) Patent No.: US 8,575,341 B2
(45) Date of Patent: Nov. 5, 2013

(54) COSMETIC COMPOSITION, COSMETIC TREATMENT METHOD, AND COMPOUND

(75) Inventors: Nathalie Mougin, Paris (FR); Xavier Schultze, Les Pavillons Sous Bois (FR); Anne-Claude Dublanchet, Antony (FR); Michel Philippe, Wissous (FR)

(73) Assignee: L'Oreal, Paris (FR)

( * ) Notice: Subject to any disclaimer, the term of this patent is extended or adjusted under 35 U.S.C. 154(b) by 32 days.

(21) Appl. No.: 13/002,093

(22) PCT Filed: Jun. 18, 2009

(86) PCT No.: PCT/FR2009/051164
§ 371 (c)(1),
(2), (4) Date: Apr. 26, 2011

(87) PCT Pub. No.: WO2010/001041
PCT Pub. Date: Jan. 7, 2010

(65) Prior Publication Data
US 2011/0189118 A1    Aug. 4, 2011

Related U.S. Application Data

(60) Provisional application No. 61/080,284, filed on Jul. 14, 2008.

(30) Foreign Application Priority Data

Jul. 4, 2008  (FR) .................... 08 54553

(51) Int. Cl.
*C07D 403/00* (2006.01)
*A61K 8/00* (2006.01)
*A61K 8/18* (2006.01)
*A61Q 5/00* (2006.01)
*A61Q 9/00* (2006.01)

(52) U.S. Cl.
USPC .......................... 544/296; 544/209; 424/70.1

(58) Field of Classification Search
USPC ................. 544/296, 209; 424/70.1
See application file for complete search history.

(56) References Cited

U.S. PATENT DOCUMENTS 7,025,813 B2 * 4/2006 Vanmaele et al. ......... 106/31.27
7,862,805 B2   1/2011 Mougin et al.
2004/0161394 A1 * 8/2004 Mougin et al. ............ 424/70.11
2005/0031566 A1   2/2005 Cooper et al.
2010/0242188 A1 * 9/2010 Daubresse et al. ............ 8/425

FOREIGN PATENT DOCUMENTS

| EP | 1 310 533 | | 5/2003 |
|---|---|---|---|
| JP | 2009-7542 | * | 1/2009 |
| JP | 2009-215453 | * | 9/2009 |
| WO | 02 098377 | | 12/2002 |
| WO | 03 032929 | | 4/2003 |
| WO | 2004 016598 | | 2/2004 |
| WO | 2008 059125 | | 5/2008 |
| WO | WO 2008/059125 | * | 5/2008 |
| WO | WO2008/059125 | * | 5/2008 |

OTHER PUBLICATIONS

Burger's Medicinal Chemistry 336-37 (Manfred Wolf, ed., 1980).*
G.B.W.L. Ligthart, et al, Complementary Quadruple Hydrogen Bonding in Supramolecular Copolymers, 127 JACS 810 (2005).*
Tessa ten Cate, et al, Enantioselective Cyclization of Racemic Supramolecular Polymers, 125 JACS 6860 (2003).*
Valerie G.H. Lafitte, et al, Highly Stable Cyclic Dimers Based on Non-Covalent Interactions, 2006 Chem. Commun. 2173 (2006).*
International Search Report issued Apr. 6, 2010 in PCT/FR09/51164 filed Jun. 18, 2009.
Tessa Ten Cate, A et al . "Disulfide Exchange in Hydrogen-Bonded Cyclic Assemblies: Stereochemical Self-Selection by Double Dynamic Chemistry". Journal of Organic Chemistry. vol. 70, No. 15, pp. 5799-5803, XP002517553, (2005).
Lafitte, G. H. Valerie et al "Highly stable cylic dimmers based on non-covalent interactions", The Royal Society of Chemistry, Chemical Communications, pp. 2173-2175, XP002517554, (2006).
Li, Xiao-Qiang et al., "Donor-acceptor interaction-mediated arrangement of hydrogen bonded dimmers", Tetrahedron. vol. 60, No. 37, pp. 8275-8284, XP004527614, ISSN 0040-4020, (Sep. 6, 2004).
U.S. Appl. No. 13/002,095, filed Dec. 30, 2010, Mougin, et al.

* cited by examiner

*Primary Examiner* — Sean Basquill
(74) *Attorney, Agent, or Firm* — Oblon, Spivak, McClelland, Maier & Neustadt, L.L.P.

(57) ABSTRACT

The invention relates to a cosmetic composition, particularly for hair care, and to a method for cosmetically treating keratin material, particularly the hair, using the compounds of Formula (I), where: —n=1, 2, 3, or 4; —R1, R'1, R2, and R'2 are H, —OH, —NRR', or a C1-C18 carbon group capable of containing one or more heteroatoms selected from among O, S, and N; and —Z is a multivalent carbon radical optionally substitutable and/or interruptible by specific groupings, it being understood that said radical Z includes at least one heteroatom selected from among N, O, and S.

31 Claims, No Drawings

COSMETIC COMPOSITION, COSMETIC TREATMENT METHOD, AND COMPOUND

The present invention relates to a method for cosmetic treatment of keratin materials, in particular the hair, using a composition comprising compounds capable of forming hydrogen bonds, and also to the cosmetic compositions thus prepared.

In the cosmetics industry, there is a constant desire to improve the properties of keratin materials and to combat damage, such as external attacks, for instance pollution and ultraviolet radiation, or chemical attacks, for instance those caused by dyeing or permanent-waving treatments.

Among the damage suffered by the hair, mention may in particular be made of a loss of sheen, an increased hydrophilic nature, a loss or detachment of some of the scales, and difficulties in disentangling.

In order to improve the properties of the hair, it is known practice to use compositions containing cosmetic active agents in order to provide the keratin materials, such as the hair, with all the beneficial effects associated with these cosmetic active agents. However, the persistence and therefore the effectiveness of these active agents are not sufficient, since they can be easily removed with shampoo, or alternatively they do not form a homogeneous deposit at the surface of the hair.

The object of the present invention is to propose a cosmetic composition which can be used for cosmetically treating the hair, and can give the hair long-lasting cosmetic properties.

It has in fact been noted that compounds comprising entities capable of forming physical interactions with one another can give the hair advantageous cosmetic qualities. These compounds are in particular characterized by the presence of at least one entity capable of giving at least 3 hydrogen bonds, in particular 4 hydrogen bonds, and also by their low mass.

The subject of the present invention is therefore a cosmetic composition comprising, in a cosmetically acceptable medium, at least one compound of formula (I):

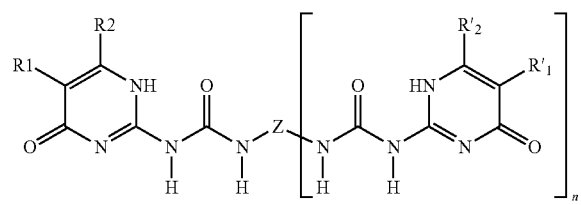

in which:
n=1, 2, 3 or 4;
R1, R'1, R2 and R'2, which may be identical or different within one and the same formula, represent H, —OH, —NRR' (with R and R', which may be identical or different, being H or a linear or branched C1-C12 alkyl radical); or a linear, branched and/or cyclic, saturated or unsaturated, optionally aromatic, C1-C18 carbon-based, in particular alkyl, group which can contain one or more heteroatoms chosen from O, S and N;
Z is a multivalent radical, which is divalent to pentavalent depending on the value of n, chosen from:
(i) a linear or branched, saturated or unsaturated, C1 to C32 carbon-based, in particular hydrocarbon-based, radical, optionally interrupted or substituted, one or more times, with an optionally aromatic C3-C12 (hetero)cycle; or
(ii) an optionally aromatic C3-C12 (hetero)cyclic carbon-based, in particular hydrocarbon-based, radical, optionally substituted with one or more linear or branched, saturated or unsaturated, C1 to C32 carbon-based, in particular hydrocarbon-based, radicals;
it being possible for said Z radical to be:
substituted with 1 to 12 (inclusive) groups chosen from —OH, —SO₃R, —OSO₃R, —SO₃H, —OSO₃H, —COOH, —COOR, —CONRR' and —N⁺RR'R", with R, R' and R"=C1-C12 alkyl, in particular methyl; and/or
interrupted with 1 to 5 (inclusive) groups chosen from:
(i) the following divalent groups: —S—, —NH— (or =NH), —O—, —C(O)—, —SO₂—,

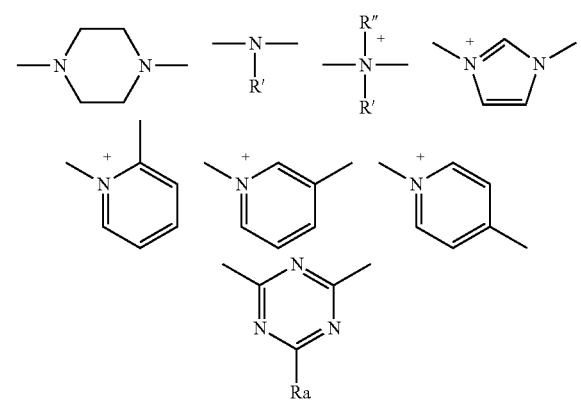

with
Ra=H or halogen, in particular Cl, or C1-C6 alkyl, and
R' and R", which may be identical or different, representing a hydrogen atom or a linear, branched and/or cyclic, saturated or unsaturated, carbon-based, in particular alkyl, radical containing 1 to 22 carbon atoms, (i) optionally substituted with one or more groups chosen from —SO₃R₁, —OSO₃R₁, —COOR₁, —Si(OR₁)₃, —N⁺R₁R₂R₃ or —NR₁R₂, in which R₁, R₂ and R₃, independently of one another, are chosen from H and C1-C22, in particular C1-C12, alkyl, preferably methyl; and/or (ii) optionally interrupted with one or more groups chosen from —NH, —O— and —C(O)— (alone or in combination);
(ii) the following trivalent groups:

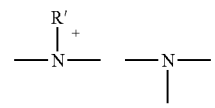

R' being as defined above for the divalent groups, said trivalent groups being generally present at the junction of said radicals (in particular when Z is trivalent);
it being understood that said Z radical comprises at least one heteroatom chosen from N, O and S.

Another subject of the invention is a method for cosmetically treating keratin materials, which comprises applying such a cosmetic composition to said keratin materials.

The compounds of formula (I) constitute yet another subject of the invention.

It has been noted that depositing a compound according to the invention onto the hair or causing a compound according to the invention to penetrate into the hair makes it possible to provide the hair with a beneficial effect. Without being bound by the present explanation, it is possible to imagine that ureidopyrimidone entities are capable of generating, in situ in or on the hair, a crosslinked network by physical associations between molecules. When deposited on the hair or the skin, said compound becomes involved in and trapped in a crosslinked deposit, which increases its remanence, in particular with respect to sebum, water and shampoo. Moreover, since the crosslinking is a physical crosslinking, it is possible for the effect to be persistent while at the same time allowing the compound to be removed during make-up removal. The removal of the deposit can in particular consist of rinsing with a cleansing composition applied at ambient temperature or at a higher temperature, or using a make-up remover, or by using any known agent for breaking hydrogen bonds.

The present invention can in particular make it possible to hydrate and reinforce keratin materials, and to provide long-lasting softness and sheen, such that the effect remains perceptible after at least one shampooing operation.

The term "reinforcement of keratin materials" is intended to mean in particular an improvement in the mechanical properties, which may result in:

an increase in their rigidity, which gives them greater strength and body; or else a decrease in their deformation, in particular under wet conditions, which allows the hair to readily return to its initial shape once dried, and results in an improvement in the dynamics of the hair; or else better resistance to tensile mechanical forces which are applied thereto, for example during combing, and which can lead to breaking of the hair.

Moreover, to be able to treat the hair in situ can also make it possible to bring protective and repair properties to the hair, following a dyeing, bleaching, permanent-waving, smoothing or hair straightening treatment.

Creating this crosslinked network in the hair also makes it possible to avoid premature bleeding of a dye.

The compounds according to the invention can therefore both coat the hair, and therefore provide in particular reinforcement properties, and also penetrate into the hair and provide, in situ, protection or repair properties, in particular.

Many compounds which incorporate ureidopyrimidone (UPY) units have been described in the literature and studied for their self-assembling property by fundamental research laboratories. However, none of these documents describes the application of these compounds to keratin materials, nor even the possible use thereof for reinforcing said materials.

In the cosmetics field, mention may be made of WO 02098377 which describes, in general, compounds comprising UPY units for cosmetic applications to the skin and the hair. Mention may also be made of WO 2003032929, which describes the preparation of supramolecular polymers and the use thereof in hair applications. Mention may also be made of WO 2004016598, which describes the preparation of supramolecular polymers and the use thereof in varied applications, including cosmetic applications. Alternatively, mention may be made of WO 2005042641, which describes the preparation of supramolecular polymers, in particular of polyurethane type, and the use thereof in varied applications, including cosmetic applications.

In all these documents, the compounds described are polymers, and therefore high-molecular-weight compounds, which will not therefore penetrate into the hair in order to provide it with beneficial properties, in particular in terms of protection of the hair.

The compound which can be used in the context of the invention therefore corresponds to formula (I):

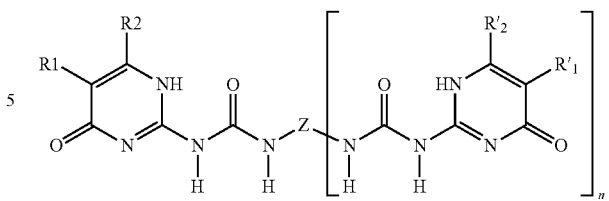

in which:

n=1, 2, 3 or 4; preferably n=1 or n=2;

R1, R'1, R2 and R'2, which may be identical or different within one and the same formula, represent H, —OH, —NRR' (with R and R', which may be identical or different, being H or a linear or branched C1-C12, preferably C1-C4, alkyl radical, and better still a methyl or ethyl radical); or a linear, branched and/or cyclic, saturated or unsaturated, optionally aromatic, C1-C18, preferably C1-C12, carbon-based, in particular alkyl, group which can contain one or more heteroatoms chosen from O, S and N; these heteroatoms can in particular be present in the form of an OH, COOH and/or NRR' radical.

The R1, R2, R'1 and R'2 radicals can in particular be chosen from:

H;

NH$_2$;

a C1-C18 alkyl group, optionally substituted or interrupted with a quaternary ammonium radical, and/or optionally substituted with one or more amino (NH$_2$), ester (COOH) and/or hydroxyl (OH) functions;

a C4-C12 cycloalkyl group, optionally substituted with one or more amino (NH$_2$), ester (COOH) and/or hydroxyl (OH) functions;

a C4-C12 aryl group, optionally substituted with one or more amino (NH$_2$), ester (COOH) and/or hydroxyl (OH) functions; and/or optionally substituted with one or more PEG groups of formula —(CH$_2$CH$_2$O)$_m$— with m=2 to 15;

a C1-C4 alkoxy group;

an aryl(C1-C4)alkoxy group, optionally substituted with one or more amino (NH$_2$), ester (COOH) and/or hydroxyl (OH) functions.

Preferably, R1 and/or R'1 represent(s) H.

Preferably, R2 and/or R'2 represent(s) H, CH$_3$, C$_7$H$_{15}$, C$_{13}$H$_{27}$ or aryl, preferably methyl;

Z represents a multivalent radical (divalent to pentavalent, according to the value of n), chosen from:

(i) a linear or branched, saturated or unsaturated, C1 to C32 carbon-based, in particular hydrocarbon-based (in particular alkyl) radical, optionally interrupted or substituted, one or more times, with an optionally aromatic C3-C12 (hetero)cycle; or (ii) an optionally aromatic, C3-C12 (hetero)cyclic carbon-based, in particular hydrocarbon-based (in particular alkyl), radical, optionally substituted with one or more linear or branched, saturated or unsaturated, C1 to C32 carbon-based, in particular hydrocarbon-based, radicals;

it being possible for said radical to optionally be:

substituted with 1 to 12 groups chosen from —OH, —SO$_3$R, —OSO$_3$R, —SO$_3$H, —OSO$_3$H, —COOH, —COOR, —CONRR' and —N$^+$RR'R", with R, R' and R"=C1-C12 alkyl, in particular methyl; and/or interrupted with 1 to 5 (inclusive), in particular 1 to 4, or even 1 to 3 at most, groups chosen from:

(i) the following divalent groups: —S—, —NH— (or =NH), —O—, —C(O)—, —SO$_2$—,

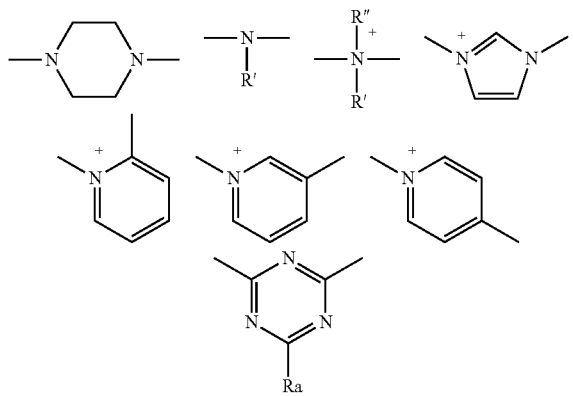

with

Ra=H or halogen, in particular Cl, or C1-C6 alkyl, and

R' and R", which may be identical or different, representing a hydrogen atom or a linear, branched and/or cyclic, saturated, carbon-based, in particular alkyl, radical containing 1 to 22 carbon atoms, (i) optionally substituted with one or more groups chosen from —$SO_3R_1$—, —$OSO_3R_1$—, —$COOR_1$—, —$Si(OR_1)_3$, —$N^+R_1R_2R_3$ or —$NR_1R_2$, in which $R_1$, $R_2$ and $R_3$, independently of one another, are chosen from H and C1-C22, in particular C1-C12, alkyl, preferably methyl; and/or (ii) optionally interrupted with one or more groups chosen from —NH—, —O— and —C(O)— (alone or in combination):

(ii) the following trivalent groups:

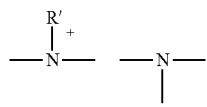

R' being as defined above for the divalent groups, said trivalent groups being generally present at the junction of said radicals (in particular when Z is trivalent);

it being understood that said Z radical comprises at least one heteroatom chosen from N, O and S, preferably chosen from N and S, and even better still at least one nitrogen heteroatom.

The Z radical may preferably be a saturated, linear or branched, (divalent to pentavalent) alkyl radical containing 1 to 32, in particular 2 to 18, or even 3 to 12, carbon atoms, it being understood that it comprises, in addition, at least one heteroatom chosen from N, O and S, in particular in the form of a substitution or interruption group as defined above.

Preferably, said heteroatom may be present in the chain in the form of the following substitution groups: —COOH, —COOMe or —CONRR', and/or in the form of the following interruption groups: S, O, —NR'—, —$N^+(R')(R'')$— or N(trivalent). In particular, the heteroatoms may be present in the form of a combination such as, for example, —C(O)O—, —OC(O)O—, —NR'C(O)—, —NR'C(O)NR"—, —NR'C(O)O—, —NRSO$_2$— or —NR—SO$_2$—NR'—, or even in the form —(CH$_2$CH$_2$O)$_x$— with x=2 to 5. Preferably, R' and R" represent H or a C1-C12 alkyl radical, in particular a methyl or ethyl radical.

The compounds of formula (I) may correspond most particularly to the following structure (R1=R'1=H):

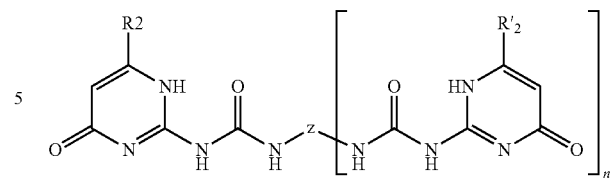

And even better still to the structures hereinafter:

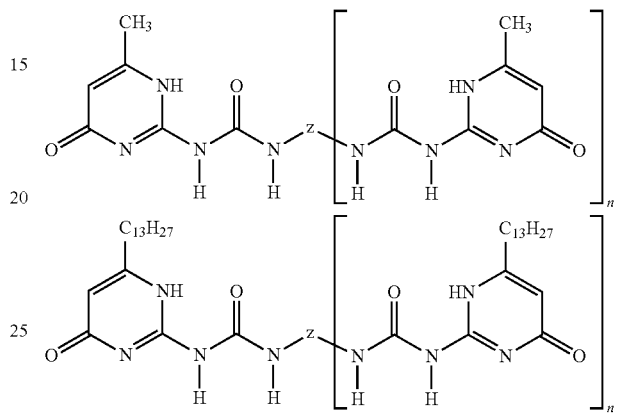

in which Z and n are as defined above, with preferably n=1.

Preferably, the Z radical represents a linear or branched, saturated or unsaturated, divalent or trivalent C1 to C32 hydrocarbon-based radical comprising at least one unit of the type: —O—; —NR'—, —$N^+R'R''$—, —S—, —C(O)O—, —OC(O)O—, —NR'C(O)—, —NR'C(O)NR"—, —NR'C(O)O— or —(CH$_2$CH$_2$O)$_x$—; with R' and R" chosen from hydrogen, or a C3-C7 cycloalkyl or linear or branched C1-C22 alkyl chain.

Most particularly, when n=1, the divalent Z radical can be chosen from the following radicals:

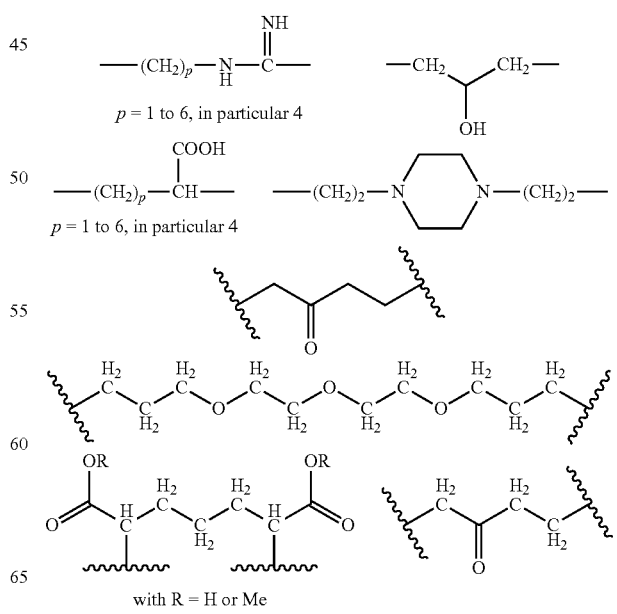

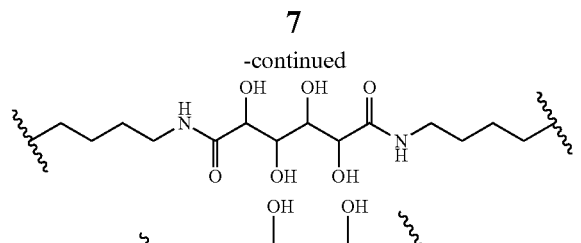
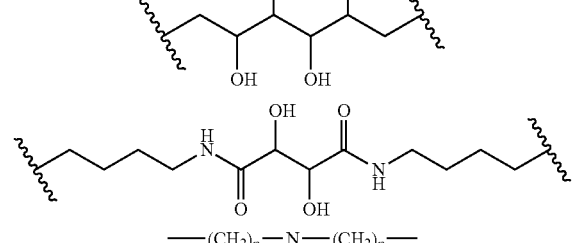
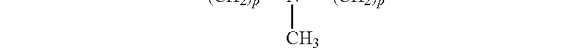
p = 1 to 6, in particular 2 or 3
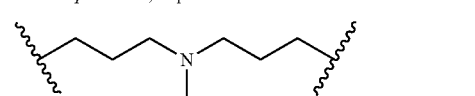
n = 1 to 4
p = 1 to 6, in particular 2 or 3
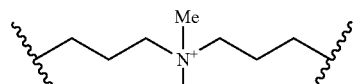
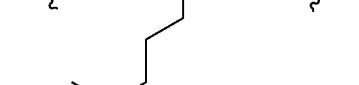
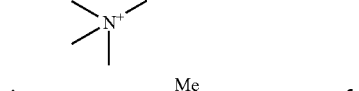
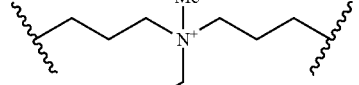
n = 1 to 2
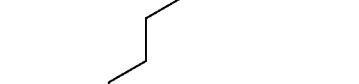
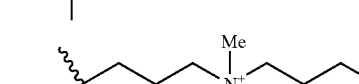
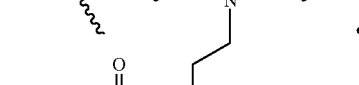
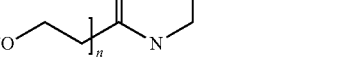
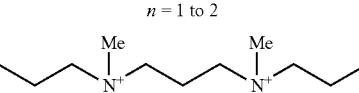
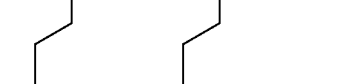
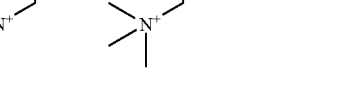
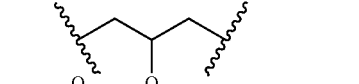
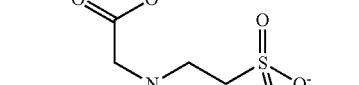
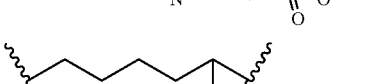
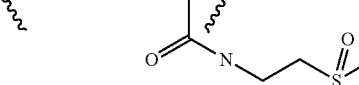
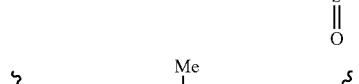
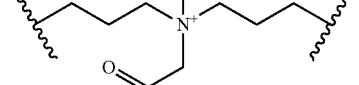
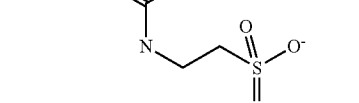

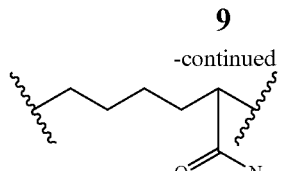
When n=2, the compound of formula (I) preferably has the following structure:
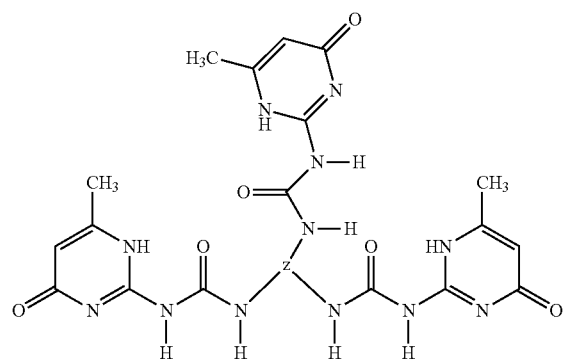
and trivalent Z can preferably be chosen from:
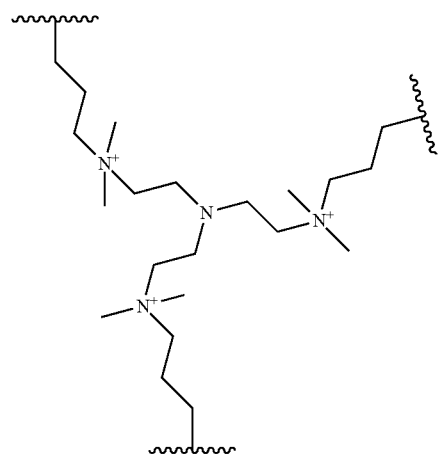
with p=1 to 6, in particular 2 or 3.
Among the compounds of formula (I) which may be advantageous, mention may be made of the following compounds:
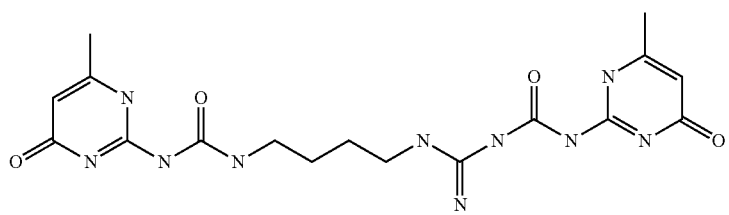
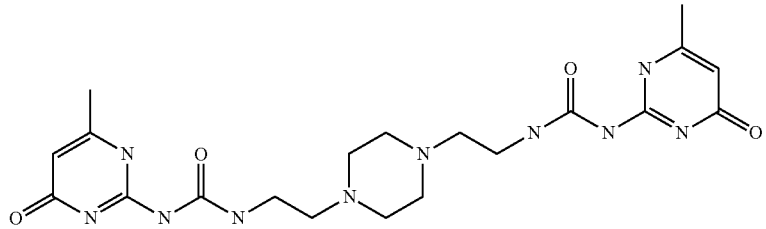
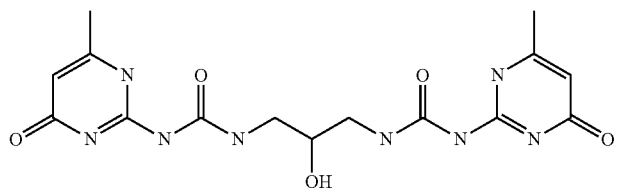
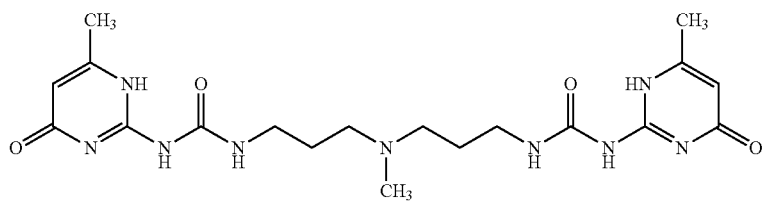

-continued
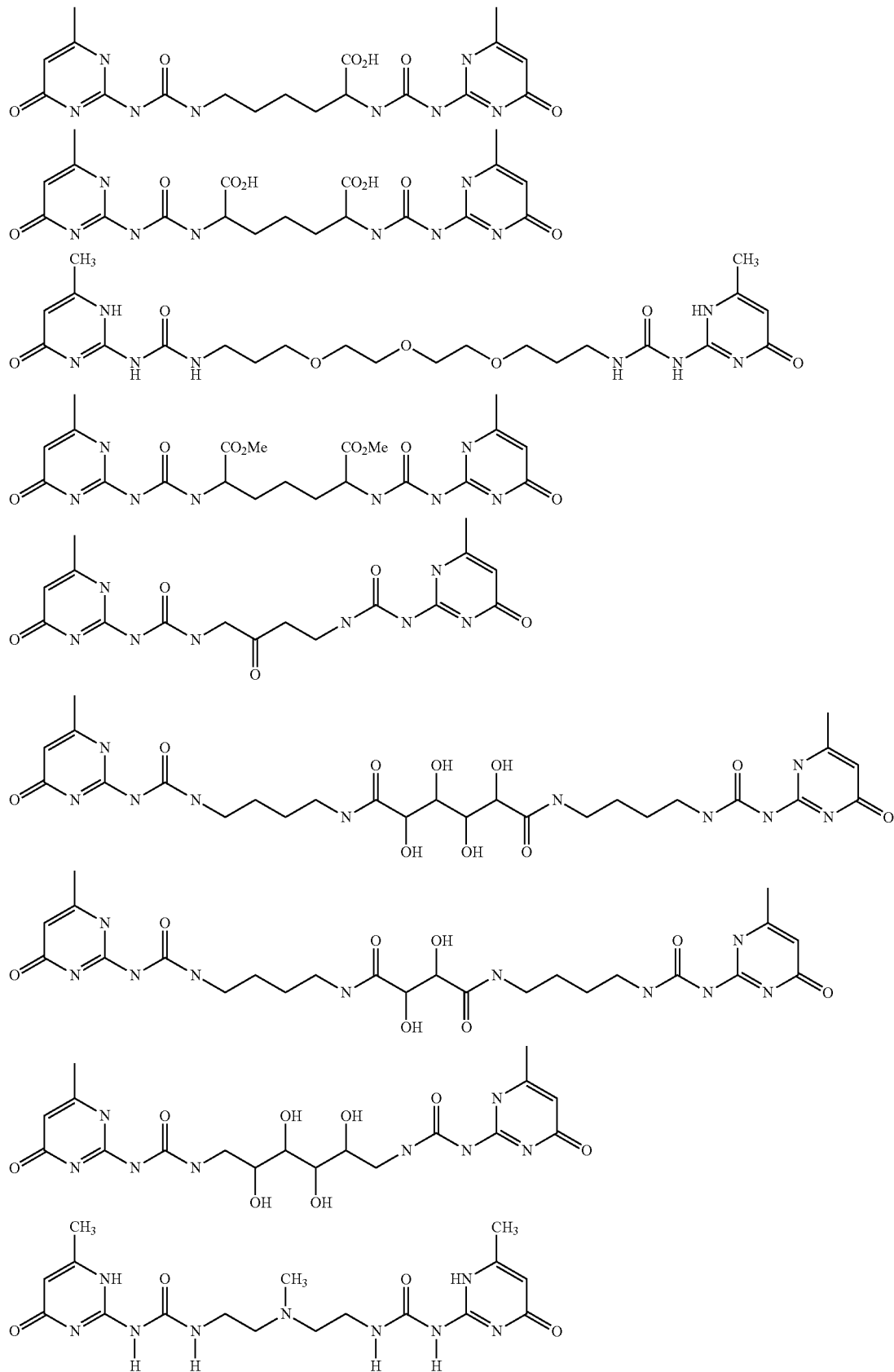

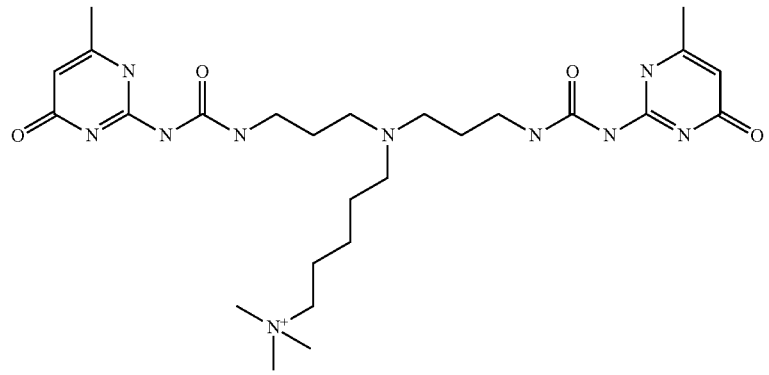
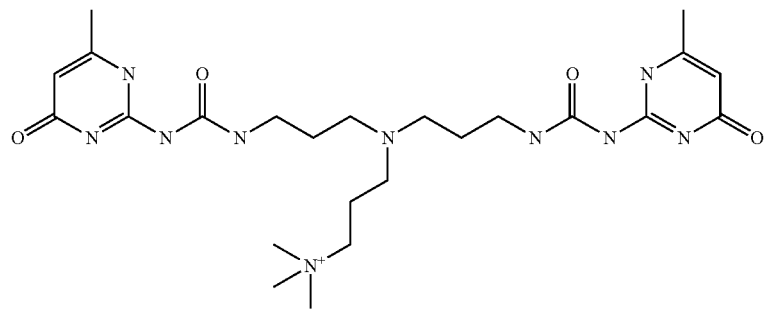
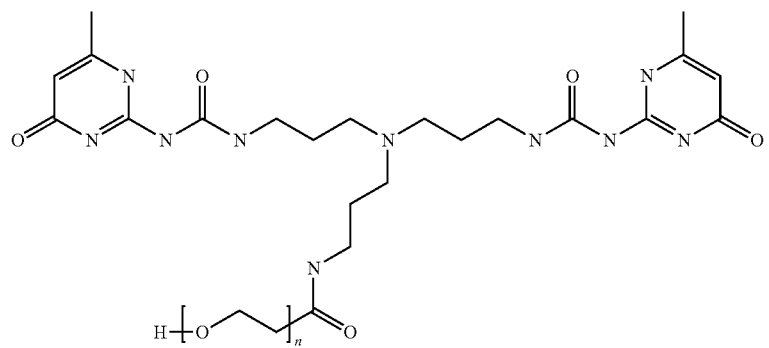
with n = 1 to 4
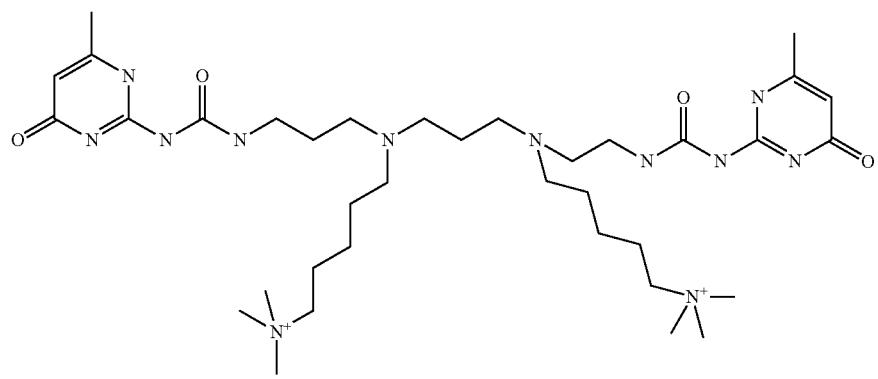
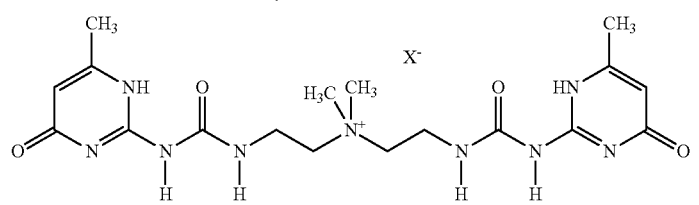

-continued
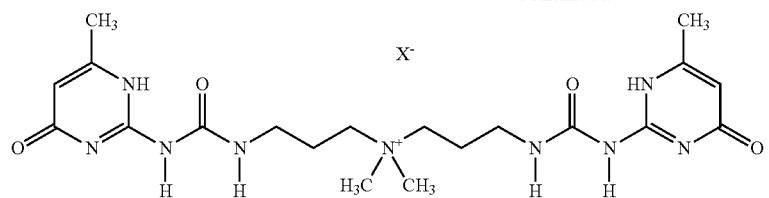
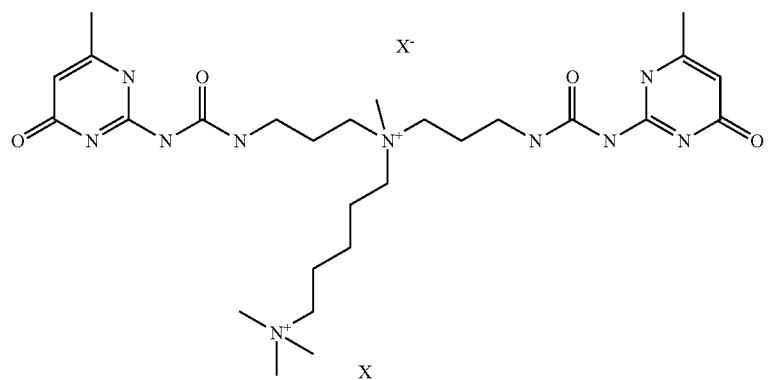
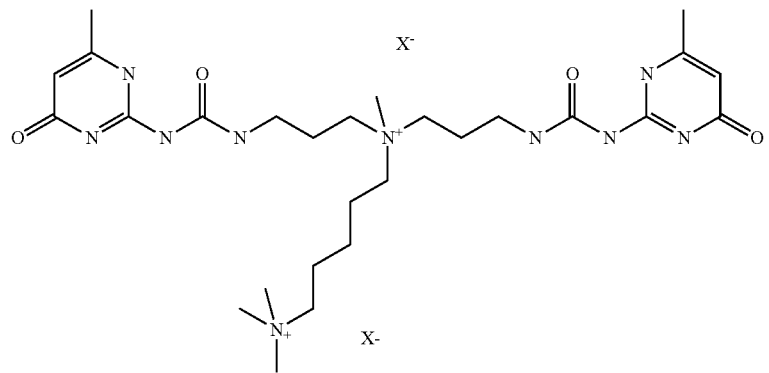
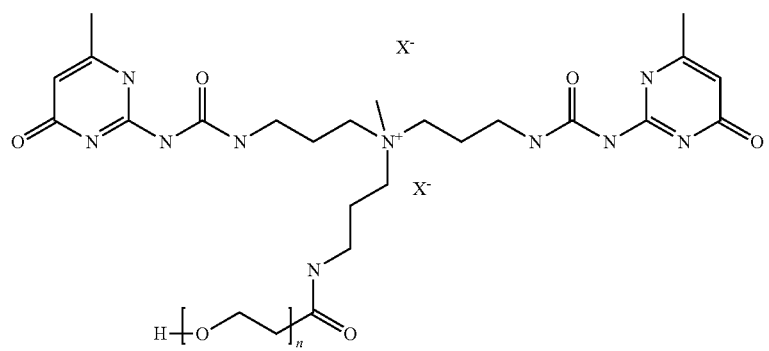
with $n$ = 1 to 4

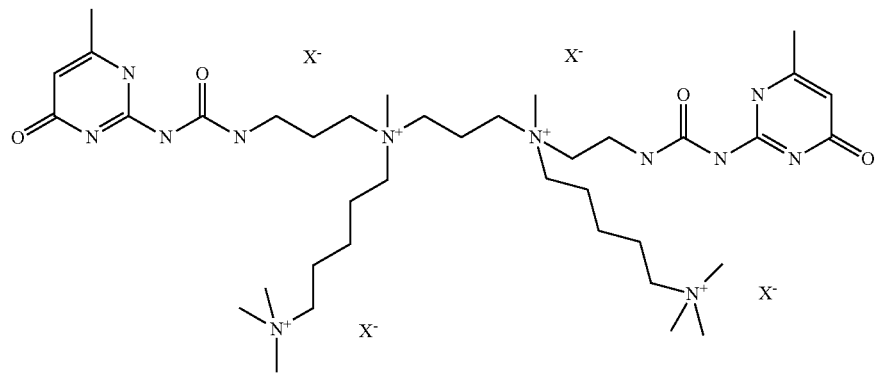
with X = Cl or Br
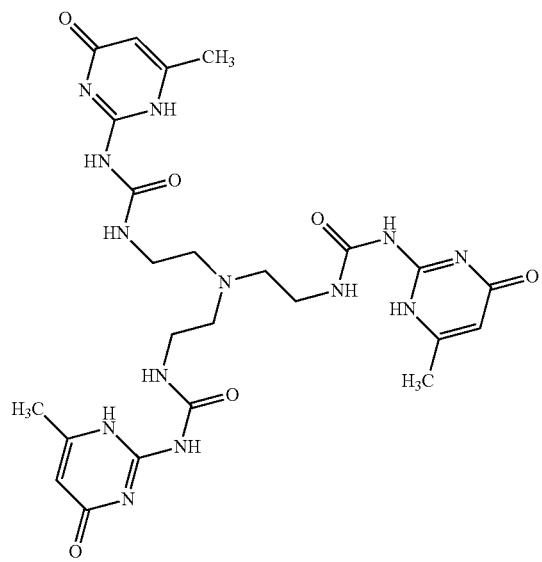
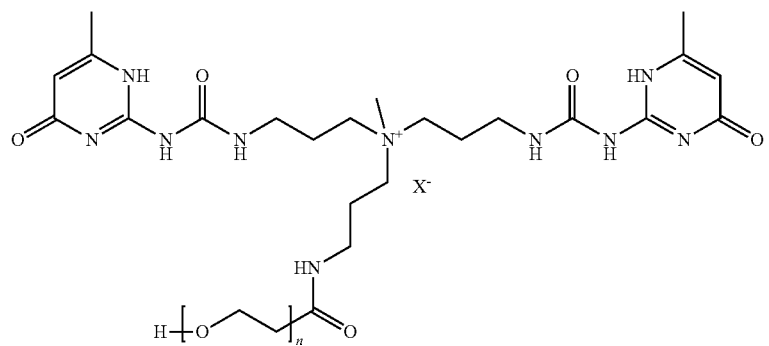
with n = 1 to 4

-continued
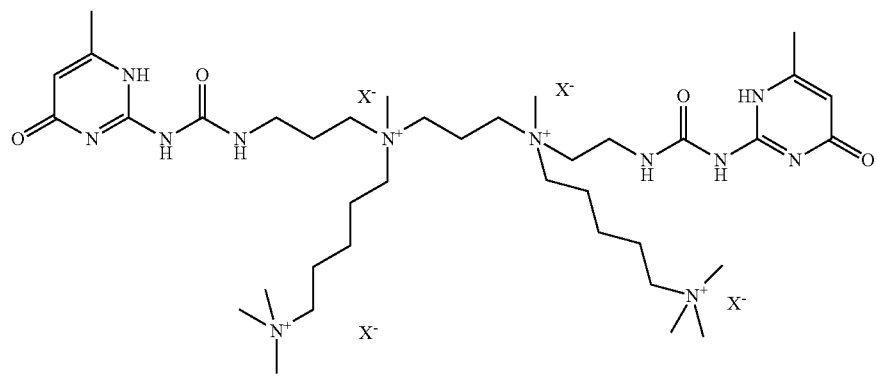
with X = Cl or Br
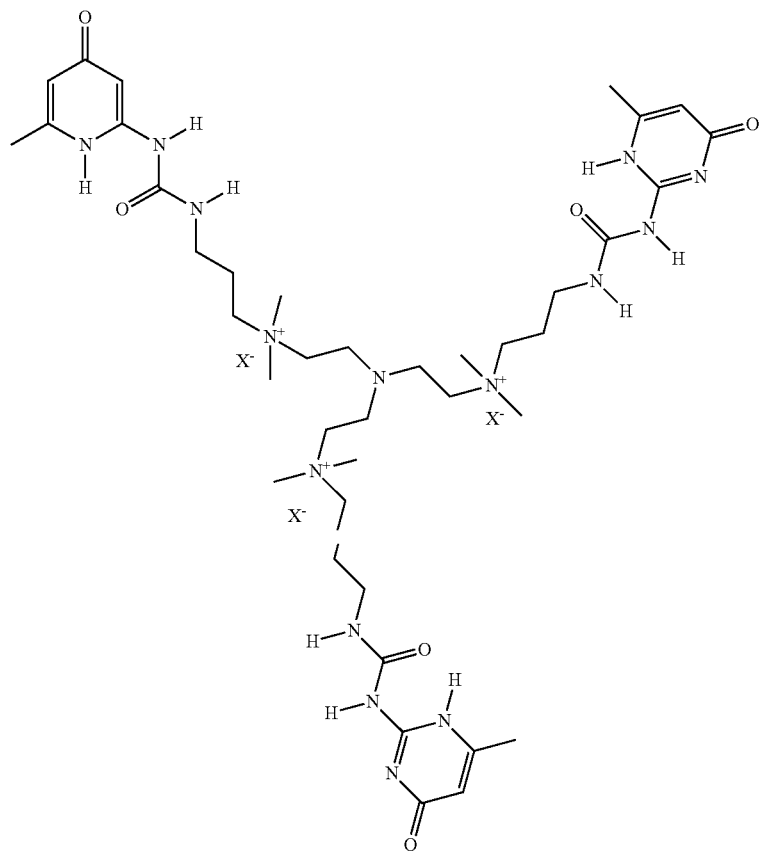
with X = Cl or Br
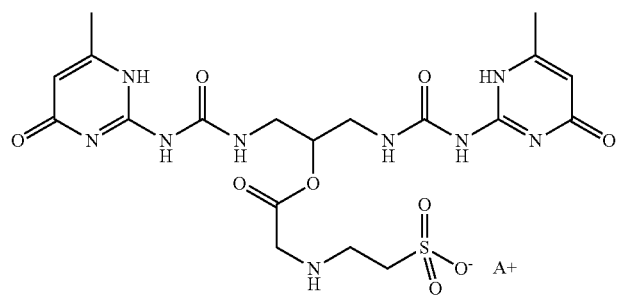
A+ = Na+, K+, NH4+

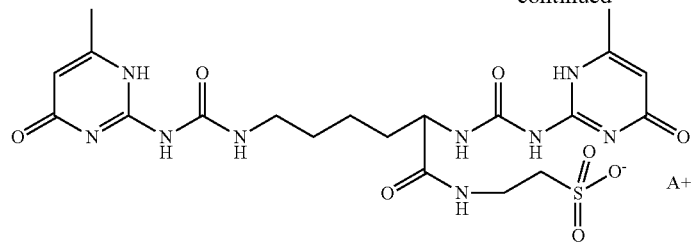
A+ = Na+, K+, NH4+
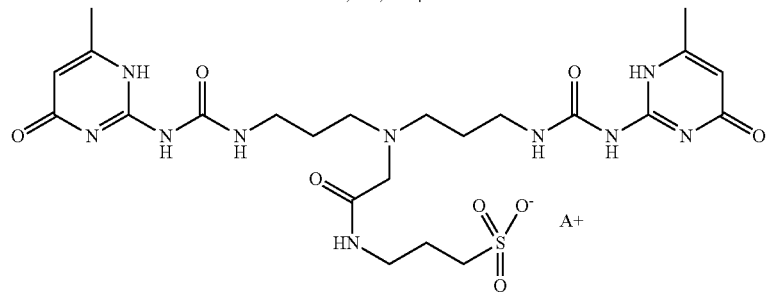
A+ = Na+, K+, NH4+
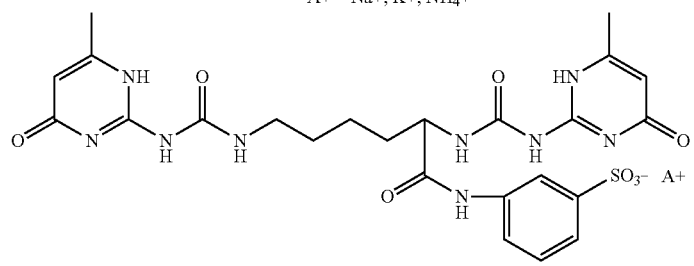
A+ = Na+, K+, NH4+
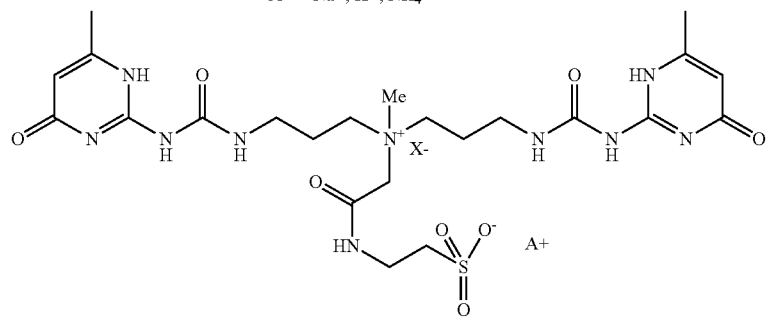
A+ = Na+, K+, NH4+
X- = Cl-, Br-
The compounds of formula (I) which are most particularly preferred are:
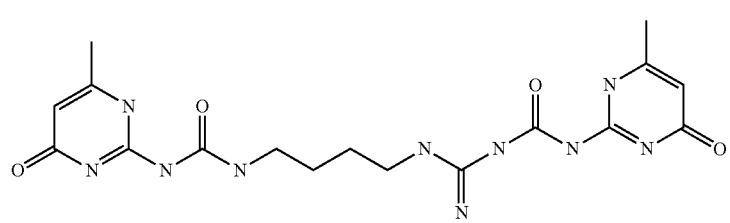

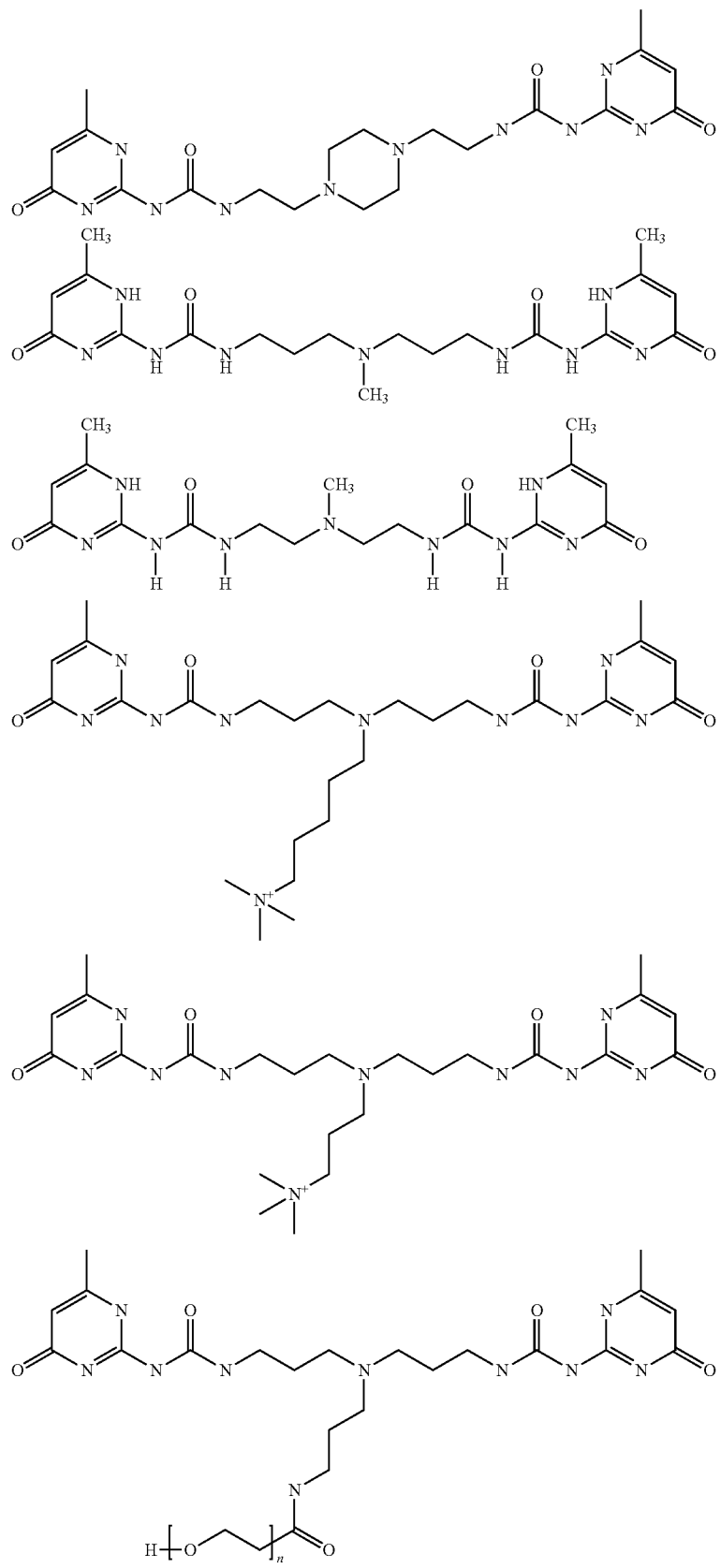
with $n$ = 1 to 4

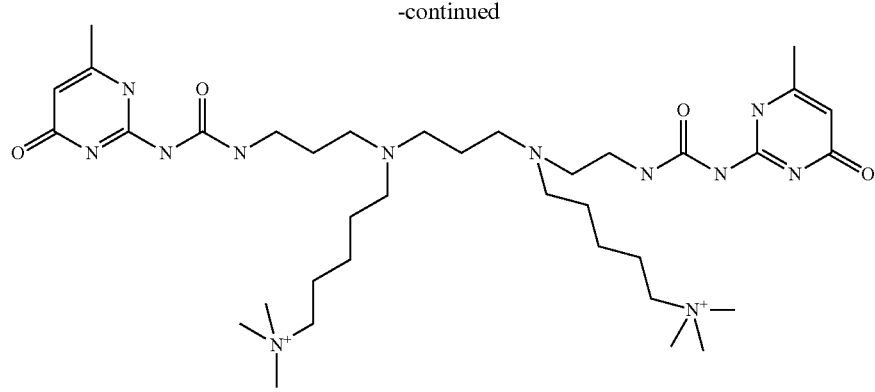
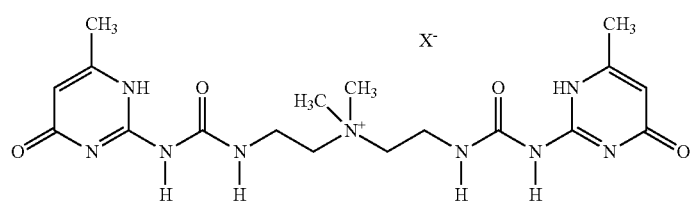
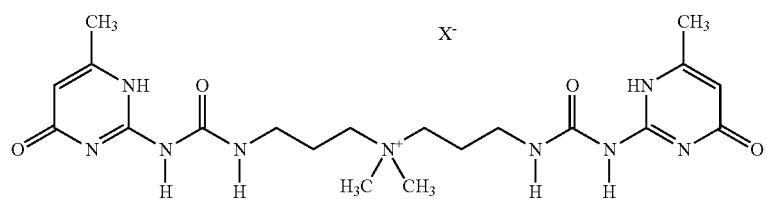
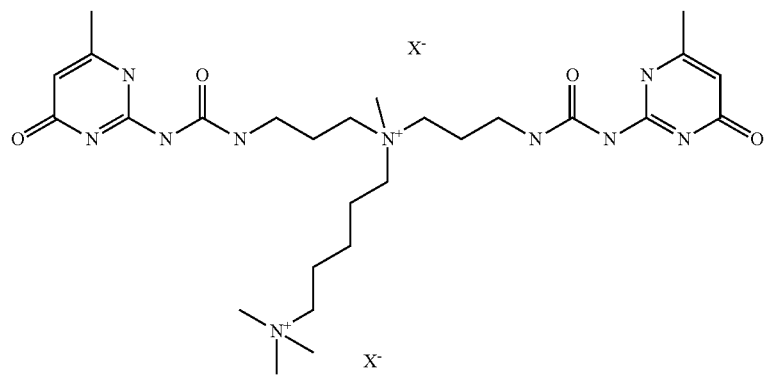
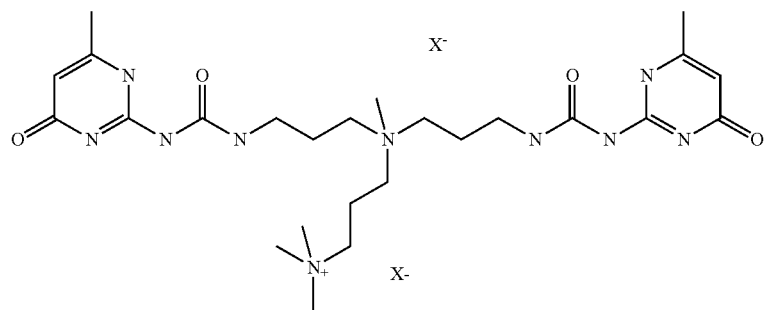

-continued
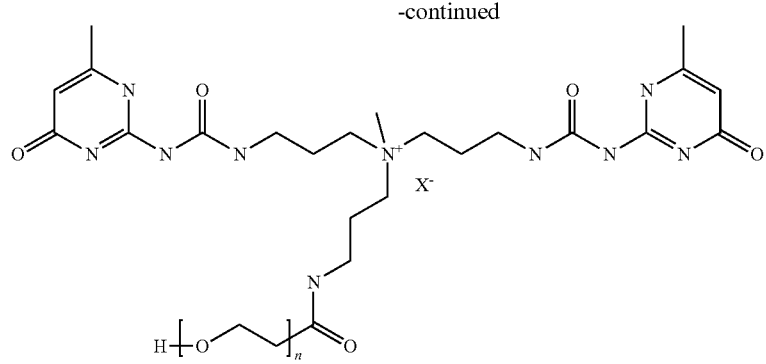
with n = 1 to 4
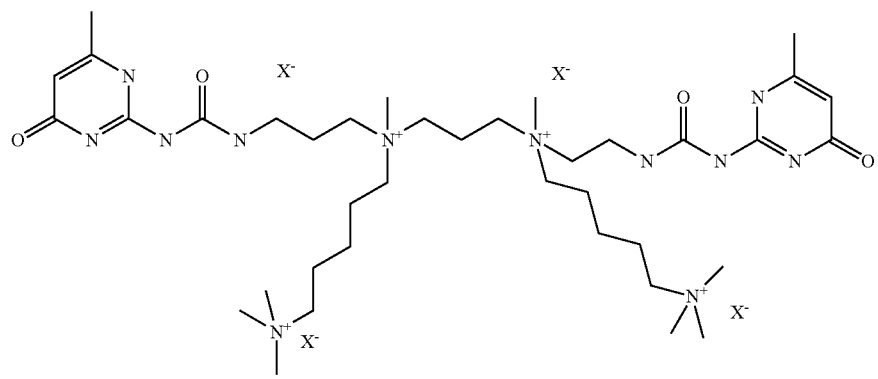
with X = Cl or Br
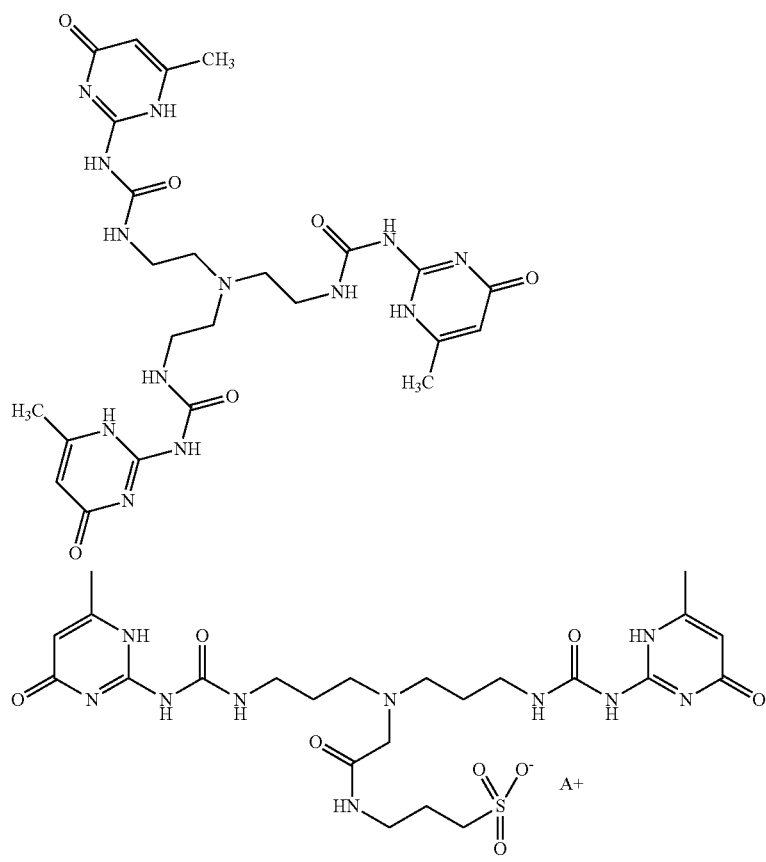
A+ = Na+, K+, NH4+

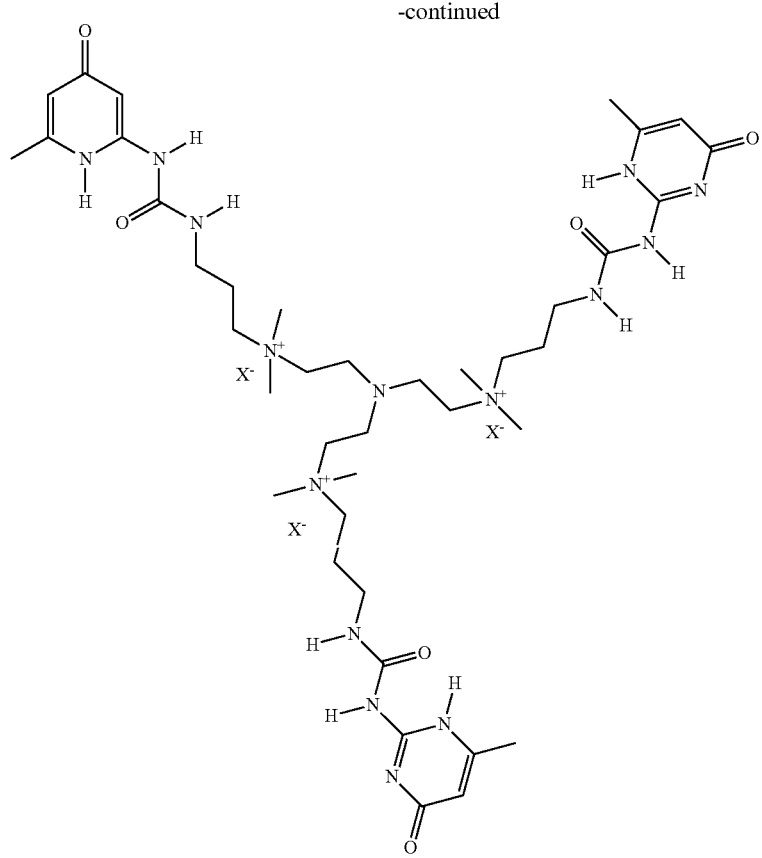
with X = Cl or Br
and also the following compounds:
N,N"-[(6-chloro-1,3,5-triazine-2,4-diyl)bis(imino-butane-4,1-diyl)]bis[3-(6-methyl-4-oxo-1,4-dihydro-pyrimidin-2-yl)urea]:
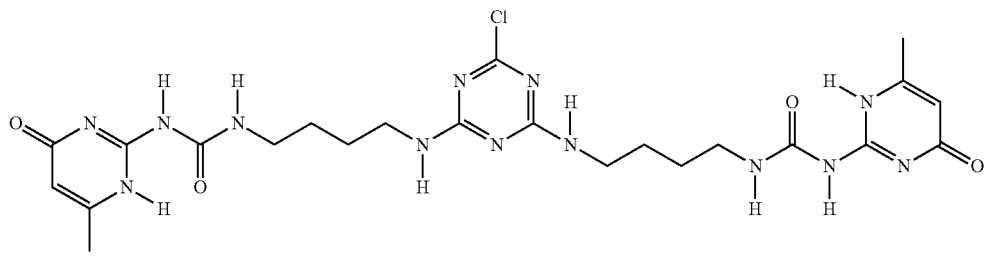 [SMILES: Cc1cc(=O)nc(NC(=O)NCCCCNc2nc(Cl)nc(NCCCCNC(=O)Nc3nc(=O)cc(C)[nH]3)n2)[nH]1]
2-[bis(2{[(6-methyl-4-oxo-1,4-dihydropyrimidin-2-yl)-carbamoyl]oxy}ethyl)amino]ethanesulphonic acid:
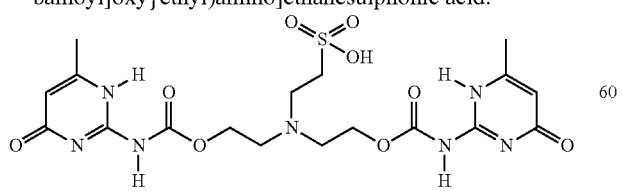
3-amino-N-methyl-N,N-bis(3-{[(6-methyl-4-oxo-1,4-dihydropyrimidin-2-yl)carbamoyl]amino}propyl)propan-1-aminium chloride:

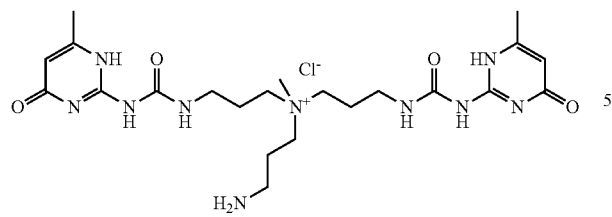

N,N,N',N'-tetramethyl-N-(2-{[(6-methyl-4-oxo-1,4-dihydropyrimidin-2-yl)carbamoyl]amino}ethyl)-N'-(3-{[(6-methyl-4-oxo-1,4-dihydropyrimidin-2-yl)carbamoyl]-amino}propyl)ethane-1,2-diaminium dichloride:

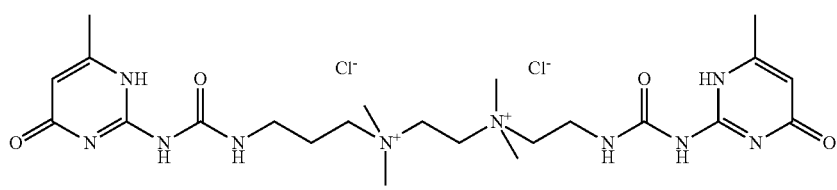 [SMILES: Cc1cc(=O)nc(NC(=O)NCCC[N+](C)(C)CC[N+](C)(C)CCNC(=O)Nc2nc(=O)cc(C)[nH]2)[nH]1 ; [Cl-] ; [Cl-]]

N-methyl-N,N-bis(3-{[(6-methyl-4-oxo-1,4-dihydro-pyrimidin-2-yl)carbamoyl]amino}propyl)oct-7-en-1-aminium chloride:

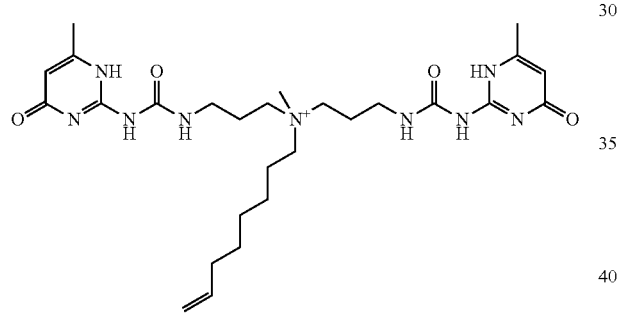

9-(acryloyloxy)-N-methyl-N,N-bis(3-{[(6-methyl-4-oxo-1,4-dihydropyrimidin-2-yl)carbamoyl]amino}propyl)nonan-1-aminium chloride:

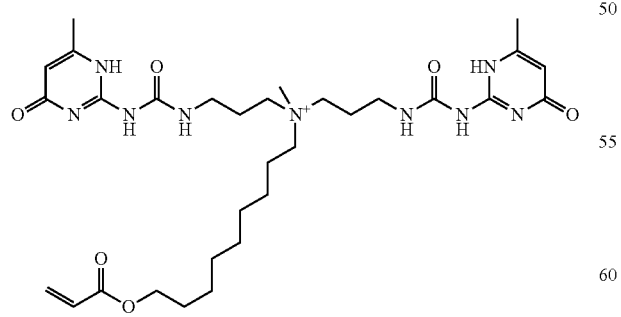

N',N'''-cyclohexane-1,2-diylbis[1-(6-methyl-4-oxo-1,4-dihydropyrimidin-2-yl)urea]:

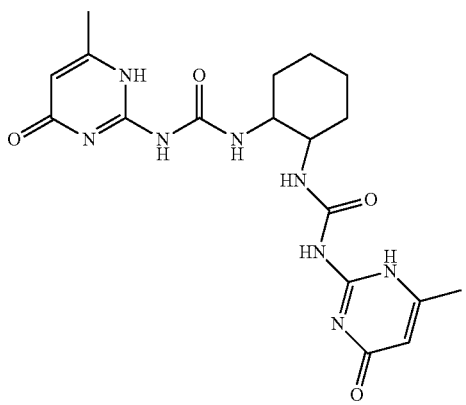 [SMILES: Cc1cc(=O)nc(NC(=O)NC2CCCCC2NC(=O)Nc2nc(=O)cc(C)[nH]2)[nH]1]

Preferably, the weight-average molecular weight (Mw) of the compound according to the invention is less than or equal to 1200 g/mol. This low molecular weight promotes in particular the penetration of the compounds into the hair.

The compounds of formula (I) can be prepared according to any of the known methods.

If the following group is referred to as A:

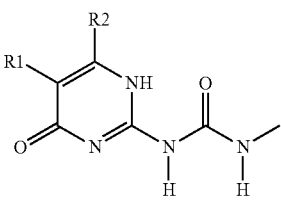

the compounds according to the invention can therefore be represented schematically in the following way: A-Z-(A)$_n$.

They can be obtained during reaction:

between a reactive function bonded to the group A and a reactive function borne by the group Z; or else between a reactive function bonded to a precursor of the group A and a reactive function borne by the group Z so as to simultaneously form the group A and the entity A-Z;

the two reactive functions being, of course, capable of reacting with one another and it being possible for them to be bonded directly or via a divalent segment to the group A and/or to the group Z and/or to the precursor of said group A.

The reactive functions can preferably be chosen from the following functions:

isocyanate —N=C=O;
isothiocyanate —N=C=S;
carboxylic acid or ester —COOR$_a$ or activated ester COOR$_b$ with R$_a$ being H or a linear or branched, $C_1$-$C_{12}$, preferably $C_1$-$C_4$ alkyl radical, and better still a methyl or ethyl radical; and OR$_b$ being chosen from phenoxy, 4-nitrophenoxy, 2,4,5-trichlorophenoxy and the following radicals:

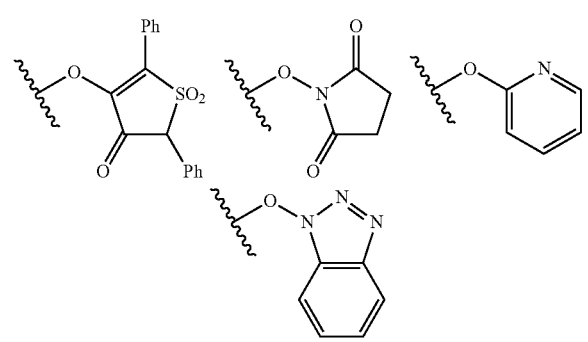

acyl halide,
acyl imidazole or acyl benzotriazole of formula:

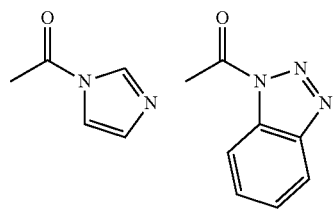

acid anhydride,
activated carbamic acid —NHCOX with X=Cl, imidazole, or OR$_b$ with OR$_b$ as defined above;
hydroxyl (OH) or activated hydroxyl, for example in O-tosylate form,
primary or secondary amine —N(R$_a$)$_2$, with R$_a$, which may be identical or different, being as defined above;
a function chosen from:

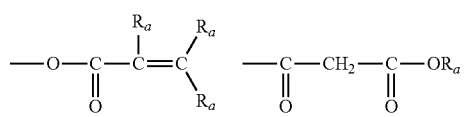

with R$_a$, which may be identical or different, being as defined above.

Preferably, the reactive functions that are a precursor of the bond between Z and A are chosen from isocyanate, amine or hydroxyl functions or functions of the formula:

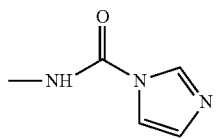

A particular method for obtaining A-Z— is the one described in the article by Katritzky et al., Comprehensive Organic Functional Group Transformations, Pergamon: Oxford, 1995, vol. 6, pp. 500-506 or else in Arkiv der Pharmazie, 314(1), 34-41, 1981.

It is in particular possible to react:

an isocytosine B with an activated carbamic acid:

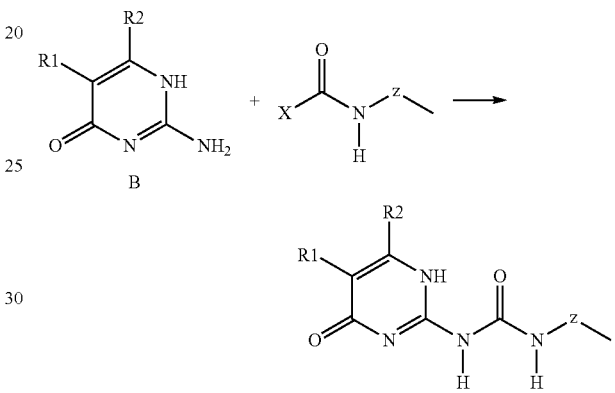

an isocytosine B with an amine-derived isocyanate:

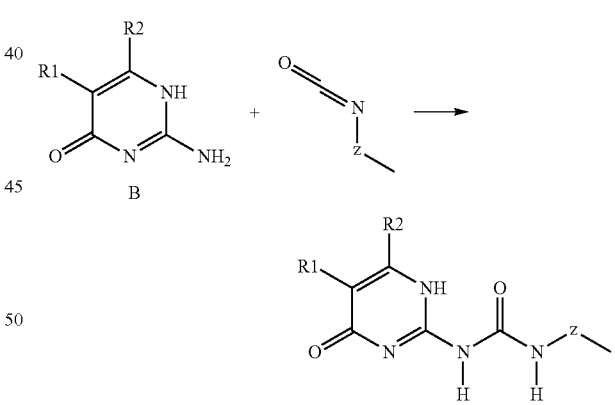

an isocytosine comprising an activated carbamic function C, with an amine:

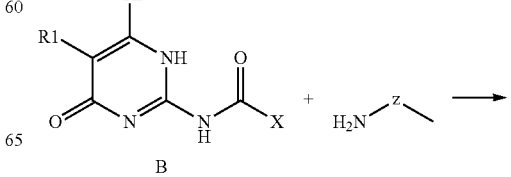

-continued

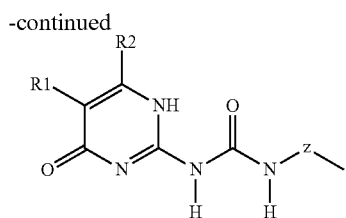

a β-keto ester D with a guanylalkylurea derivative E:

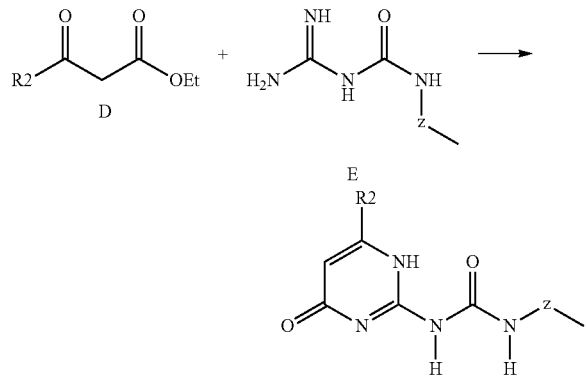

Another method for preparing A-Z— consists in synthesizing a compound of the following type:

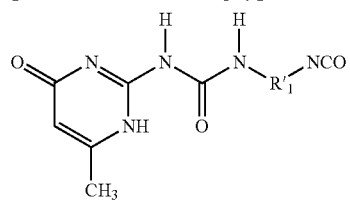

and then reacting it with an alcohol or an amine.

The divalent group R'1 represents, for example, a group chosen from: 1,2-ethylene, 1,6-hexylene, 1,4-butylene, 1,6-(2,4,4-trimethylhexylene); 1,4-(4-methylpentylene), 1,5-(5-methylhexylene), 1,6-(6-methylheptylene); 1,5-(2,2,5-trimethylhexylene), 1,7-(3,7-dimethyloctylene); isophorone; 4,4'-methylene-biscyclohexylene, tolylene, 2-methyl-1,3-phenylene; 4-methyl-1,3-phenylene; 4,4-biphenylenemethylene; and preferably isophorone; —(CH$_2$)$_2$—; —(CH$_2$)$_6$—; —CH$_2$CH(CH$_3$)—CH$_2$—C(CH$_3$)$_2$—CH$_2$—CH$_2$; 4,4'-methylenebiscyclohexylene; 2-methyl-1,3-phenylene. Preferably, R'1=isophorone or 1,6-hexylene.

Particularly preferably, the compounds of formula (I) are soluble or dispersible in water or soluble in water basified using a 28% aqueous ammonia solution (the pH of the solution is then between 8 and 10).

The term "soluble" is intended to mean that the compound forms a clear solution, at a concentration of 1% by weight in the medium, at 25° C. and 1 atm.

The term "dispersible" is intended to mean that the compound forms in the medium, at a concentration of 1% by weight at 25° C. and 1 atm, a stable suspension or dispersion of fine particles, which are generally spherical. The term "stable" is intended to mean that the suspension does not precipitate and does not therefore display any visible deposit. The average size of the particles constituting the suspension or the dispersion is preferably less than 1 μm, and more generally ranges between 5 and 400 nm, preferably 10 to 250 nm. These particle sizes are measured by any conventional light scattering method.

The compounds according to the invention find a most particular application in the cosmetics field, in particular in the hair-related field.

The amount of compound present in the cosmetic compositions of the invention depends, of course, on the type of composition and on the desired properties, and can vary within a very wide range, generally between 0.001% and 15% by weight, preferably between 0.005% and 10% by weight, in particular between 0.01% and 8% by weight, or even between 0.1% and 7% by weight, relative to the total weight of the composition.

The cosmetic compositions can of course comprise a mixture of compounds of formula (I).

The compositions according to the invention may be in any of the galenical forms conventionally used, and in particular in the form of an aqueous, alcoholic or aqueous-alcoholic, or oily solution or suspension; a solution or a dispersion of the lotion or serum type, an emulsion, in particular of liquid or semi-liquid consistency, of the O/W, W/O or multiple type; a suspension or emulsion of soft consistency of cream type (O/W) or (W/O); an aqueous or anhydrous gel, or any other cosmetic form. Preferably, the composition is in the form of an aqueous suspension, serum or lotion.

These compositions can be packaged, in particular in pump dispensers or in aerosol containers, in order to apply the composition in vaporized form (lacquer) or in the form of a mousse. Such packaging forms are indicated, for example, when it is desired to obtain a spray or a mousse, for treating the hair. In these cases, the composition preferably comprises at least one propellant.

The compositions according to the invention comprise a cosmetically acceptable medium, i.e. a medium which is compatible with keratin materials, in particular the skin of the face or of the body, the lips, the hair, the eyelashes, the eyebrows and the nails.

Said medium preferably comprises at least one customary cosmetic ingredient, in particular chosen from propellants; water, carbon-based oils; silicone oils; C8-C40 alcohols, C8-C40 esters, C8-C40 acids; C1-C7 alcohols, ketones, organic solvents, nonionic surfactants, cationic surfactants, anionic surfactants, amphoteric surfactants, zwitterionic surfactants; sunscreens; moisturizers; antidandruff agents; antioxidants; reducing agents; oxidation bases, couplers, oxidizing agents, direct dyes; hair-straightening agents, pearlescent and opacifying agents; plasticizers or coalescence agents; hydroxy acids; pigments; fillers; silicones; thickeners; emulsifiers; polymers; urea, and agents for producing a basic pH. Said medium can of course comprise several cosmetic ingredients appearing in the list above.

Depending on their nature and the purpose of the composition, the customary cosmetic ingredients can be present in normal amounts, which can be readily determined by those skilled in the art, and which can, for each ingredient, be from 0.01% to 80% by weight.

The composition can in particular comprise water, one or more C1-C7 alcohols, alone or as a mixture with water, and in particular a water/ethanol, water/isopropanol or water/benzyl alcohol mixture.

The carbon-based, in particular hydrocarbon-based, oils and/or the silicone oils can be present in a proportion of from 0.01% to 20% by weight, in particular 0.02% to 10% by weight, relative to the total weight of the composition. Mention may in particular be made of hydrogenated or nonhydrogenated plant, animal or mineral oils, saturated or unsaturated, linear or branched, cyclic or aliphatic, hydrocarbon-based synthetic oils, for instance poly(alpha-olefin)s, in particular polydecenes and polyisobutenes; water-soluble or water-insoluble, organomodified or nonorganomodified, volatile or nonvolatile silicone oils; fluoro or perfluoro oils; mixtures thereof.

The alcohols, the esters and the acids, having 8 to 40 carbon atoms, can be present in a proportion of from 0.01% to 50% by weight, in particular 0.1% to 20% by weight, relative to the total weight of the composition.

Mention may in particular be made of C12-C32, in particular C12-C26, linear-chain or branched-chain fatty alcohols, and in particular cetyl alcohol, stearyl alcohol, cetylstearyl alcohol, isostearyl alcohol, octyldodecanol, 2-butyloctanol, 2-hexyldecanol, 2-undecylpentadecanol, oleyl alcohol or linoleyl alcohol.

Mention may also be made of alkoxylated, in particular ethoxylated, C8-C40, in particular C16-C20, fatty alcohols, preferably comprising from 10 to 50 mol of ethylene oxide and/or of propylene oxide, such as oleth-12, ceteareth-12 and ceteareth-20, oxypropylenated stearyl alcohol, in particular comprising 15 mol of propylene oxide, oxyethylenated lauryl alcohol, in particular comprising more than 7 oxyethylenated groups, and also mixtures thereof.

Mention may also be made of C16-C40 linear-chain or branched-chain fatty acids, and in particular 18-methyleicosanoic acid, coconut oil or hydrogenated coconut oil acids; stearic acid, lauric acid, palmitic acid and oleic acid, behenic acid, and mixtures thereof.

Mention may also be made of C16-C40 linear-chain or branched-chain fatty esters, such as esters of polyols derived from fatty acids containing from 8 to 30 carbon atoms, and the oxyalkylenated, and in particular oxyethylenated, derivatives thereof, the polyols preferably being chosen from sugars, C2-C6 alkylene glycols, glycerol, polyglycerols, sorbitol, sorbitan, polyethylene glycols, polypropylene glycols, and mixtures thereof.

The nonionic, cationic, anionic, amphoteric or zwitterionic surfactants, and also mixtures thereof, can be present in a proportion of from 0.01% to 50% by weight, in particular 0.05% to 40% by weight, or even 0.1% to 30% by weight, relative to the total weight of the composition.

The propellants can be present in a proportion of from 5% to 90% by weight, relative to the total weight of the composition, and more particularly in a proportion of from 10% to 60% by weight.

The sunscreens can be present in a proportion of from 0.01% to 20% by weight, in particular 0.5% to 10% by weight, relative to the total weight of the composition.

The moisturizers can be present in a proportion of from 0.01% to 20% by weight, in particular 0.1% to 7% by weight, relative to the total weight of the composition.

The antidandruff agents can be present in a proportion of from 0.001% to 20% by weight, in particular 0.01% to 10% by weight, relative to the total weight of the composition, preferably 0.1% to 5% by weight.

The antioxidants can be present in a proportion of from 0.05% to 1.5% by weight, relative to the total weight of the composition.

The reducing agents can be present in a proportion of from 0.1% to 30% by weight, in particular 0.5% to 20% by weight, relative to the total weight of the composition.

The oxidation bases can be present in an amount of between 0.001% and 10% by weight, preferably from 0.005% to 6% by weight, relative to the total weight of the composition.

The couplers can be present in an amount of between 0.001% and 10% by weight, preferably from 0.005% to 6% by weight, relative to the total weight of the composition.

The oxidizing agents can be present in an amount of between 1% and 40% by weight, preferably between 1% and 20% by weight, relative to the weight of the composition.

The direct dyes can be present in an amount of between 0.001% and 20% by weight, preferably from 0.01% to 10% by weight, relative to the total weight of the composition.

The hair-straightening agents can be present in a proportion of from 0.01% to 3.5% by weight, in particular 0.05% to 1.5% by weight, relative to the total weight of the composition.

The pearlescent and opacifying agents can be present in a proportion of from 0.01% to 3% by weight, in particular 0.05% to 2.5% by weight, relative to the total weight of the composition.

The plasticizers or coalescence agents can be present in a proportion of from 0.1% to 25% by weight, in particular 1% to 10% by weight, relative to the total weight of the composition.

The hydroxy acids can be present in a proportion of from 1% to 10% by weight, in particular 2% to 5% by weight, relative to the total weight of the composition.

The pigments and fillers can be present in a proportion of from 0.01% to 50% by weight, in particular 0.02% to 30% by weight, relative to the total weight of the composition.

The silicones may be volatile or nonvolatile; mention may in particular be made of modified or unmodified polyorganosiloxanes, i.e. polyorganosiloxane oils, gums and resins, as they are or in the form of solutions in organic solvents, or in the form of emulsions or microemulsions. They can be present in an amount of from 0.01% to 40% by weight, in particular 0.05% to 20% by weight, relative to the total weight of the composition.

The thickeners can be present in a proportion of from 0.01% to 10% by weight, in particular from 0.1% to 5% by weight, relative to the total weight of the composition.

The polymers, which are in particular water-soluble or soluble in carbon-based and/or silicone oils, can be present in a proportion of from 0.01% to 20% by weight, in particular 0.1% to 10% by weight, relative to the total weight of the composition.

Among the agents for producing a basic pH, mention may be made of aqueous ammonia and also the bases commonly used in the cosmetics industry.

Those skilled in the art will take care to select the ingredients which are part of the composition, and also the amounts thereof, in such a way that they are not detrimental to the properties of the compositions of the present invention.

The cosmetic composition according to the invention may be in the form of a care, cleansing and/or makeup product for the skin of the body or the face, the lips, the eyebrows, the eyelashes, the nails and the hair, a suntan or self-tanning product, a body hygiene product, a hair product, in particular a hair care, cleansing, styling, shaping or dyeing product.

It is especially of particularly advantageous use in the hair-related field, in particular for hairstyle retention or hair shaping, or caring for, cosmetically treating or cleansing the hair. The hair compositions are preferably shampoos, conditioners, styling or care gels, care lotions or creams, conditioning agents, hairsetting lotions, blow-drying lotions, setting and styling compositions, such as lacquers or sprays; hair restructuring lotions; lotions or gels for combating hair loss, antiparasitic shampoos, antidandruff lotions or shampoos, or shampoos for treating seborrhoea. It can in particular be in the form of a hair dyeing product, in particular an oxidation dyeing product, optionally in the form of a dye shampoo; in the form of a permanent-waving, hair-straightening or bleaching composition, or else in the form of a rinse-out or leave-in composition, to be applied before or after dyeing, bleaching, permanent-waving or hair-straightening, or else between the two steps of a permanent-waving or hair-straightening operation.

The composition according to the invention may also be in the form of a care, in particular moisturizing, composition for the skin of the body or of the face, the lips and/or the skin appendages, in particular a care product for use in cosmetically treating the skin, and in particular in moisturizing it, smoothing it, depigmenting it, nourishing it, and protecting it against sunlight, or conferring on it a specific cosmetic treatment. Thus, it may be a lip care base, a fixing base for lipsticks, an antisun or artificial tanning composition, a (day, night, antiageing, moisturizing) care composition for the face; a mattifying composition; a composition for cleansing the skin, for example a makeup-removing product or a bath or shower gel, or a cleansing bar or soap; a body hygiene composition, in particular a deodorant or antiperspirant product, or else a depilatory composition, or an aftershave gel or lotion. It may also be in the form of a makeup product for the skin of the body or of the face, the lips, the eyelashes, the nails or the hair; in particular a foundation, a blusher, a face powder, an eyeshadow, a concealer, an eyeliner, a mascara, a lipstick, a lip gloss, a lip pencil, a nail varnish, a nail care product or a product for temporary tattooing of body skin.

Even more particularly, the composition according to the invention has an advantageous application in the care and the cosmetic treatment, in particular the protection, of the hair, in particular weakened and/or damaged hair, for example hair weakened and/or damaged by chemical or mechanical treatments; use may in particular be made of the compounds according to the invention in post-treatment, after a hair dyeing, bleaching or straightening step.

A subject of the invention is therefore a method for cosmetically treating, in particular for making up, caring for, cleansing, dyeing or shaping keratin materials, in particular the skin of the body or of the face, the lips, the nails, the hair and/or the eyelashes, comprising the application of a cosmetic composition comprising at least one compound according to the invention to said materials.

Preferably, it is a cosmetic treatment method for conditioning the hair, in particular for giving it body and/or liveliness, or improving the disentangling, smoothing, combability, repair and manageability of the head of hair. It may be a method for repairing and/or protecting damaged or weakened hair.

In one particular embodiment of the treatment method, the composition according to the invention can be applied all at once, or preferably in several applications (multi-application).

Thus, it is possible to apply a composition comprising the compounds according to the invention, in an amount, for example, of from 0.05% to 1%, in particular 0.1% to 0.5% by weight, to the hair a first time, to leave it in for 2 to 20, in particular 10, minutes, optionally while heating at a temperature below 65° C., or else with a smoothing iron or a crimping iron, for example for a few seconds, and then, optionally, to dry the hair before applying the composition a second time, and to again leave-in for 2 to 20, in particular 10, minutes, before optionally heating at a temperature below 65° C., or else with a smoothing iron or a crimping iron, for example for a few seconds, and then to dry or allow to dry. It is possible to carry out a third application of the composition. This multi-application of the composition can in particular make it possible to improve the penetration of the compounds inside the hair, and therefore to improve the repair of the hair in situ.

In another embodiment of the method according to the invention, it is possible to apply to the hair a composition comprising the compounds according to the invention, in an amount, for example, of from 0.05% to 15%, in particular 0.5% to 10% by weight, preferably 1% to 8% by weight, to leave-in for 15 to 45, in particular 30, minutes, preferably while heating at a temperature below 65° C., or else with a smoothing iron or a crimping iron, for example for a few seconds, and then to rinse out and dry or leave to dry.

The invention is illustrated in greater detail in the following exemplary embodiments.

EXAMPLE 1

Preparation of N-(2-{methyl[2-({[(6-methyl-4-oxo-1,4-dihydropyrimidin-2-yl)amino]carbonyl}amino)ethyl]-amino}ethyl)-N'-(6-methyl-4-oxo-1,4-dihydropyrimidin-2-yl)urea

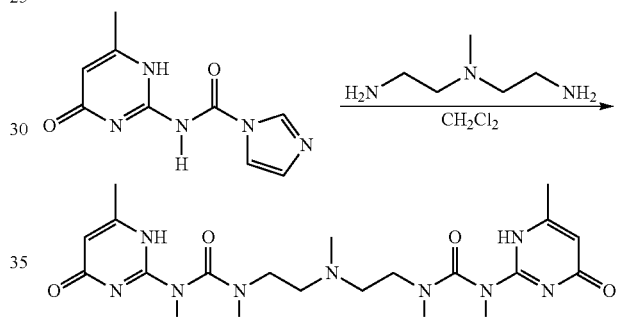

3 g of 2-(1-imidazolylcarbonylamino)-6-methyl-4[1H]-pyrimidinone (136 mmol) prepared according to the procedure described by Meijer et al., J. Am. Chem. Soc. 2003, 125, p. 6860 are added to a solution of 0.81 g of N-methyldiaminoethylamine (6.8 mmol) in 150 ml of dichloromethane. The solution is stirred at reflux for 4.5 hours. The product is precipitated from acetone, filtered off and washed with acetone, and then dried under reduced pressure.

2.43 g (5.8 mmol) of compound are obtained in the form of a white powder, hence a yield of 85%.

Melting point: 230° C.

$^1$H NMR (DMSO): δ 2.08-2.09 ppm (m, 6H), 2.22-2.24 ppm (m, 3H), 2.48-2.49 ppm (m, 4H), 3.21-3.26 ppm (m, 4H), 5.73 ppm (m, 2H); (in accordance with the expected structure).

EXAMPLE 2

Preparation of N-(6-methyl-4-oxo-1,4-dihydro-pyrimidin-2-yl)-N'-{15-[(6-methyl-4-oxo-1,4-dihydro-pyrimidin-2-yl)amino]-15-oxo-4,7,10-trioxa-14-azapenta-dec-1-yl}urea

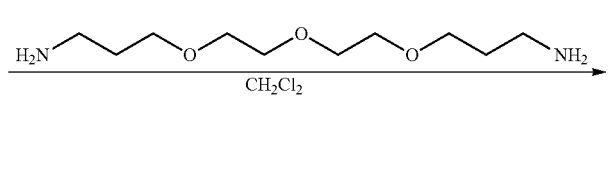

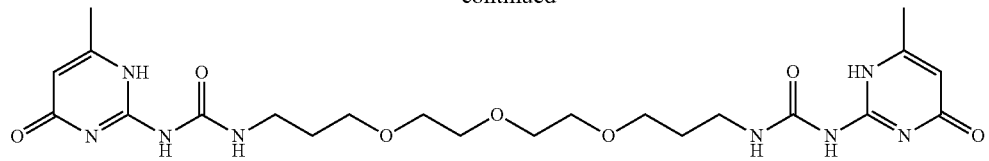

2 g of 2-(1-imidazolylcarbonylamino)-6-methyl-4[1H]-pyrimidinone (9.1 mmol) are added to a solution of 1 g of trioxamidecanediamine (4.6 mmol) in 100 ml of dichloromethane. The solution is stirred at reflux for 12 hours. The product is precipitated from acetone, filtered off and washed with acetone, and then dried under reduced pressure.

2.1 g (3.9 mmol) of compound are obtained in the form of a white powder, with a yield of 86%.

Melting point 192° C.

$^1$H NMR (DMSO): δ=2.66-1.69 ppm (m, 4H), 2.08-2.10 ppm (m, 6H), 3.16-3.20 ppm (m, 4H), 3.47-3.52 ppm (m, 12H), 5.76 ppm (m, 2H); (in accordance with the expected structure).

EXAMPLE 3

Preparation of dimethylbis{2-[3-(6-methyl-4-oxo-1,4-dihydropyrimidin-2-yl)ureido]ethyl}ammonium chloride

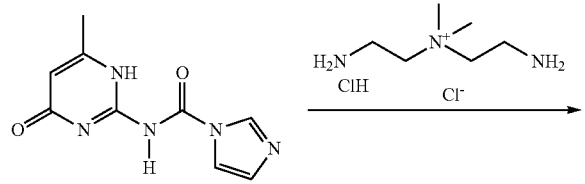

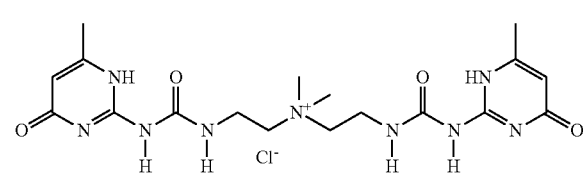

1 g of 2-(1-imidazolylcarbonylamino)-6-methyl-4[1H]-pyrimidinone is added to a solution of 0.54 g of bis(2-aminoethyl)dimethylammonium chloride dihydro-chloride (2.3 mmol) and 0.59 g of diisopropylethylamine (4.6 mmol) in 50 ml of ethanol. The solution is stirred at reflux for 24 hours. The product is precipitated from acetone, filtered off and washed with ether and then with acetone, and then dried under reduced pressure.

0.6 g (1.3 mmol) of compound is obtained in the form of a white powder, with a yield of 53%.

Melting point: 219.6° C.

$^1$H NMR (D$_2$O) δ: 2.09 ppm (s, 6H), 3.12 ppm (m, 6H), 3.40-3.46 ppm (m, 4H), 3.63-3.69 ppm (m, 4H), 5.65 ppm (m, 2H); (in accordance with the expected structure).

EXAMPLE 4

Preparation of dimethylbis{3-[3-(6-methyl-4-oxo-1,4-dihydropyrimidin-2-yl)ureido]propyl}ammonium chloride

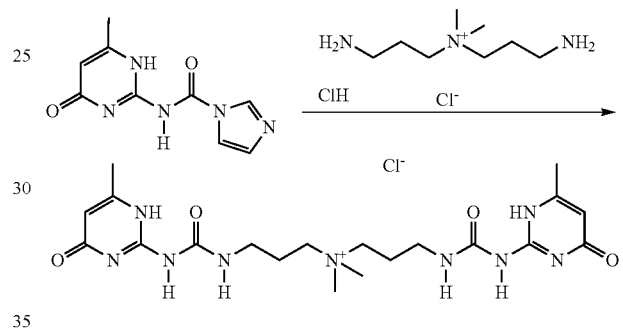

10 g of 2-(1-imidazolylcarbonylamino)-6-methyl-4[1H]-pyrimidinone are added to a solution of 6.12 g of bis(3-aminopropyl)dimethylammonium chloride dihydro-chloride (22.8 mmol) and 5.9 g of diisopropylethylamine (45.6 mmol) in 500 ml of ethanol. The solution is stirred at reflux for 24 hours. The product is precipitated from ethanol, filtered under hot conditions, and then dried under reduced pressure. 6 g (20.2 mmol) of compound are obtained in the form of a white powder, with a yield of 53%.

Melting point: 238° C.

$^1$H NMR (D$_2$O) δ: 1.70-1.95 ppm (m, 6H), 2.06-2.22 ppm (m, 6H), 3.04-3.15 ppm (m, 6H), 3.19-3.40 ppm (m, 4H), 5.60-5.78 ppm (m, 2H); (in accordance with the expected structure).

EXAMPLE 5

Preparation of N,N''-[(methylimino)dipropane-3,1-diyl]bis[N'-(6-methyl-4-oxo-1,4-dihydropyrimidin-2-yl)urea

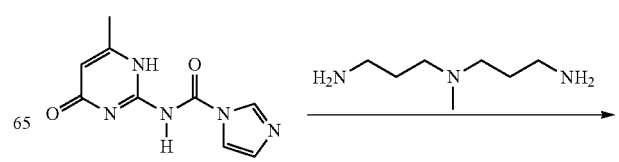

-continued

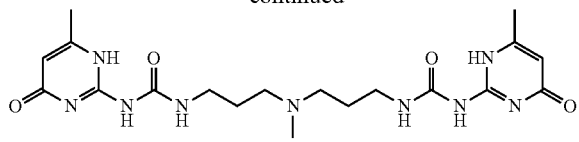

4.5 g of 2-(1-imidazolylcarbonylamino)-6-methyl-4[1H]-pyrimidinone are added to a solution of 0.99 g of N-1-(3-aminopropyl)-N-1-methylpropane-1,3-diamine (6.8 mmol) in 50 ml of dichloromethane. The solution is stirred at reflux for 48 hours. The product is precipitated from acetone, filtered off and washed with acetone, and then dried under reduced pressure.

3 g (6.7 mmol) of compound are obtained in the form of a white powder, with a yield of 98%.

Melting point: 207° C.

$^1$H NMR (DMSO) δ: 1.50-1.74 ppm (m, 4H), 1.96-2.00 ppm (s, 3H), 2.05-2.15 ppm (m, 6H), 2.16-2.21 ppm (m, 4H), 3.15-3.21 ppm (m, 4H), 5.72-5.79 ppm (m, 2H); (in accordance with the expected structure).

EXAMPLE 6

Preparation of N,N'''-({[2-({[(6-methyl-4-oxo-1,4-dihydropyrimidin-2-yl)amino]carbonyl}amino)ethyl]-imino}diethane-2,1-diyl)bis[N-(6-methyl-4-oxo-1,4-dihydropyrimidin-2-yl)urea]

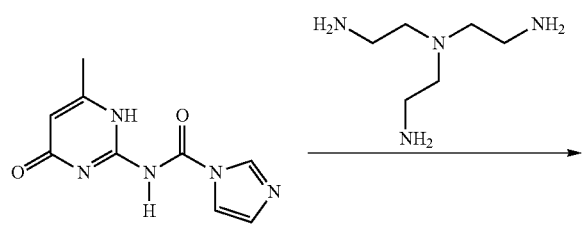

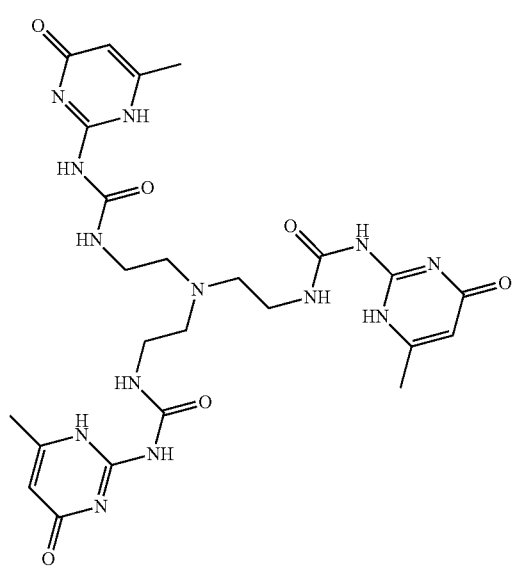

6.1 g of 2-(1-imidazolylcarbonylamino)-6-methyl-4[1H]-pyrimidinone are added to a solution of 1.2 g of tris(2-aminoethyl)amine (8 mmol) in 200 ml of dichloromethane. The solution is stirred at reflux for 24 hours. The product is precipitated from methanol, filtered off and washed with methanol, and then dried under reduced pressure.

1.2 g (2 mmol) of compound are obtained in the form of a white powder, with a yield of 24%.

Melting point: 269° C.

$^1$H NMR (DMSO): δ 2.03-2.15 ppm (m, 9H), 2.57-2.70 ppm (m, 6H), 3.18-3.27 ppm (m, 6H), 5.68-5.79 ppm (m, 3H); (in accordance with the expected structure).

EXAMPLE 7

Preparation of N,N,N,N'-tetramethyl-N',N'-bis[3-({[(6-methyl-4-oxo-1,4-dihydropyrimidin-2-yl)amino]-carbonyl}amino)propyl]pentane-1,5-diaminium dibromide

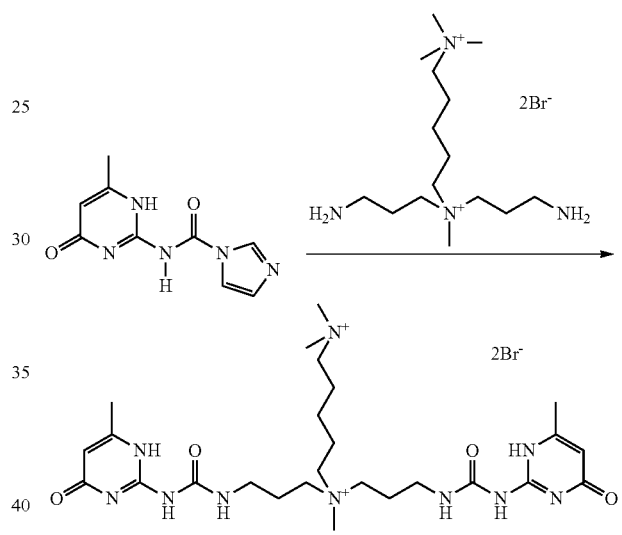

2 g of 2-(1-imidazolylcarbonylamino)-6-methyl-4[1H]-pyrimidinone (9.2 mmol) are added to a solution of 2 g of N,N-bis(3-aminopropyl)-N,N',N',N'-tetramethylpentane-1,5-diaminium dibromide (4.6 mmol) and 1.2 g of diisopropylethylamine (9.2 mmol) in 100 ml of ethanol. The solution is stirred at reflux for 5 hours. The product is precipitated from acetone. After filtration and washing with acetone, the product is dried under reduced pressure and 3.2 g (5.5 mmol) of desired compound are obtained in the form of a white powder, with a yield of 99% (hygroscopic product).

$^1$H NMR (D$_2$O): δ 1.23-1.28 ppm (m, 2H); δ 1.30-1.42 ppm (m, 2H); δ 1.69-1.85 ppm (m, 6H); δ 2.11-2.22 ppm (s, 6H); δ 3.00-3.03 ppm (s, 3H); δ 3.04-3.06 ppm (s, 9H); δ 3.09-3.21 ppm (m, 4H); δ 3.23-3.41 ppm (m, 8H); 5.66-5.84 ppm (s, 2H).

EXAMPLE 8

0.4 g of compound of Example 5 is mixed into 4 ml of water, and 1.3 ml of a 32% ammonia solution are added. The mixture is stirred for 10 minutes at 25° C. A colourless clear solution A (containing 10% dry matter) is obtained.

0.4 g of compound of Example 5 and 0.04 g of compound of Example 4 are mixed into 4 ml of water. The mixture is stirred vigorously for 12 hours at 25° C. A milky solution B is obtained.

The solutions A and B prepared above have a spontaneous pH of 8.4. Locks of hair of SA20 and SA50 type (respectively, hair with medium degree of bleaching and hair with strong degree of bleaching) are immersed in each of these solutions for 30 minutes at 65° C. The lock is wrung dry and combed, and then rinsed and dried in an oven at 60° C. for 30 minutes.

The surface condition of the treated or untreated hair is observed by laser confocal reflection microscopy.

It is noted that:
the control hair (treated with water only) has a clean appearance, with very clear scales;
the SA20 hair treated with solution A exhibits substantial coating, with a dry and cracked appearance;
the SA20 hair treated with solution B exhibits substantial coating, with a homogeneous relief;
the SA50 hair treated with solution A exhibits very substantial and even coating along the fibres;
the SA50 hair treated with solution B exhibits substantial coating, with a less homogeneous relief.

In conclusion, coating of the fibre is clearly observed with the composition according to the invention.

EXAMPLE 9

The locks of hair to be treated are soaked in a solution of 2% SLS (sodium lauryl sulphate) for 30 minutes, at 25° C.; they are then rinsed, wrung dry, and then placed in an oven (RH=45%) for 24 hours in order to dry them.

A 0.2M thioglycolic acid solution is prepared, and is adjusted to pH 9 with aqueous ammonia. The reducing solution is applied to the locks of hair (25 ml of solution for 2.5 g of hair); it is left on for 15 minutes at 30° C., and then the locks are rinsed under tap water.

A solution B' is prepared, corresponding to solution B prepared in Example 8, diluted to 0.2% by weight of compound in water. Solution B' is applied to the locks of hair (25 ml per 2.5 g of hair). The locks are left for 10 minutes at 60° C. in solution B' (step 1), and are then left for 10 minutes at 25° C. (step 2). Steps 1 and 2 are repeated 3 times. The locks are rinsed under tap water and then the hair is placed in an oven (RH=45%) for 24 hours in order to dry it.

It is noted that it is as though the hair has been repaired from the inside; it is livelier than the hair having undergone a reducing hair-shaping treatment without post-treatment with the compounds according to the invention.

EXAMPLE 10

Synthesis of N,N"-[(6-chloro-1,3,5-triazine-2,4-diyl)bis(iminobutane-4,1-diyl)]bis[3-(6-methyl-4-oxo-1,4-dihydropyrimidin-2-yl)urea]

Stage 1: Synthesis of 1-{4-[(4,6-dichloro-1,3,5-triazin-2-yl)amino]butyl}-3-(6-methyl-4-oxo-1,4-dihydropyrimidin-2-yl)urea

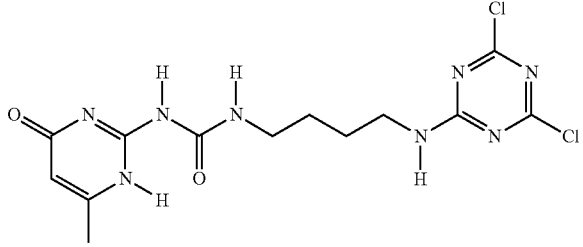

An aqueous solution (40 ml) containing 6 ml of diisopropylethylamine and 5 g (0.018 mol) of 1-(4-aminobutyl)-3-(6-methyl-4-oxo-1,4-dihydropyrimidin-2-yl)urea, prepared beforehand, was added, dropwise, to 5 g (0.018 mol) of cyanuryl chloride suspended in 80 ml of acetonitrile, at a temperature of −20° C. The reaction medium was stirred for 12 hours at ambient temperature and then poured into 200 ml of ice-cold water. The precipitate formed was filtered off and then dried under vacuum, so as to give 6.8 g (0.0175 mol) of a yellow powder with a yield of 97%.

NMR and mass spectra comply.

Stage 2: Synthesis of N,N"-[(6-chloro-1,3,5-triazine-2,4-diyl)bis(iminobutane-4,1-diyl)]bis[3-(6-methyl-4-oxo-1,4-dihydropyrimidin-2-yl)urea]

A solution containing 4.63 g (0.0168 mol) of 1-(4-aminobutyl)-3-(6-methyl-4-oxo-1,4-dihydropyrimidin-2-yl)urea and 2.17 g of diisopropylethylamine in 80 ml of acetonitrile was added, at ambient temperature, dropwise, to 6.5 g (0.0168 mol) of the product prepared above, in solution in 80 ml of acetonitrile. The reaction medium was then heated at 35° C. for 4 hours and then, after cooling to ambient temperature, poured into 200 ml of ice-cold water. The precipitate obtained was filtered off and dried, so as to give 8 g of an off-white powder, with a yield of 80%.

NMR and mass spectra comply.

The invention claimed is:

1. A cosmetic composition comprising, in a cosmetically acceptable medium, at least one compound of formula (I):

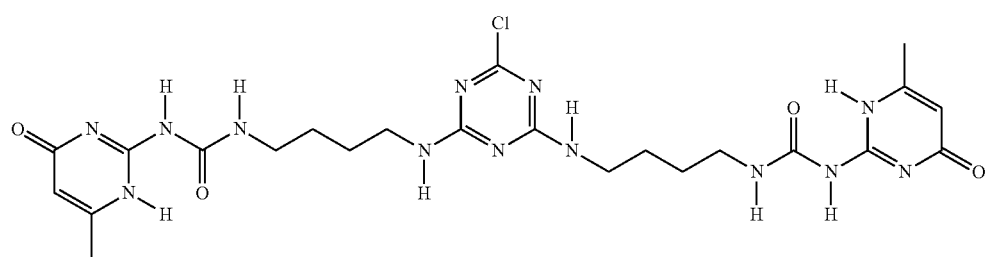

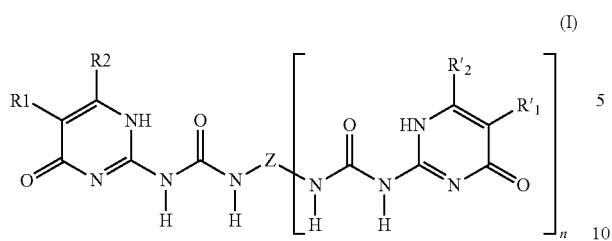

wherein:

n is 1;

R1, R'1, R2 and R'2, which may be identical or different within one and the same formula, are H, —OH, —NRR' with R and R', which may be identical or different, being H or a linear or branched C1-C12 alkyl radical; or a linear, branched and/or cyclic, saturated or unsaturated, optionally aromatic, C1-C18 carbon-based group which can contain one or more heteroatoms selected from the group consisting of O, S and N; and Z is a divalent radical selected from the group of radicals consisting of:

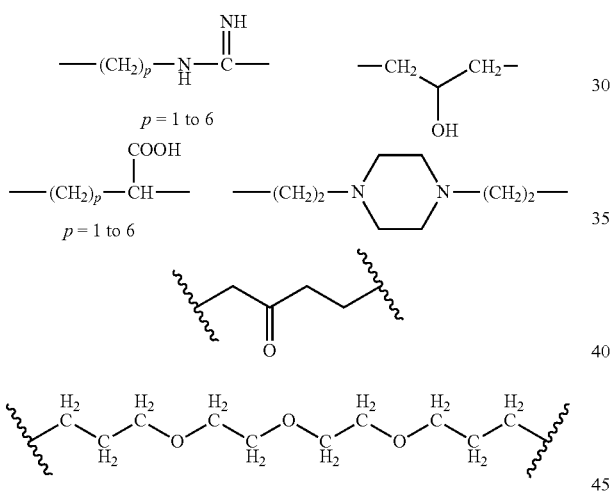

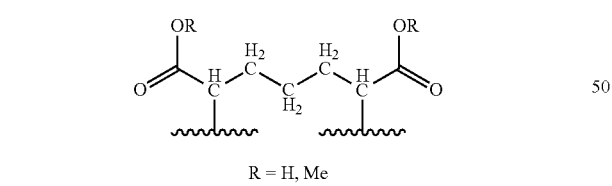

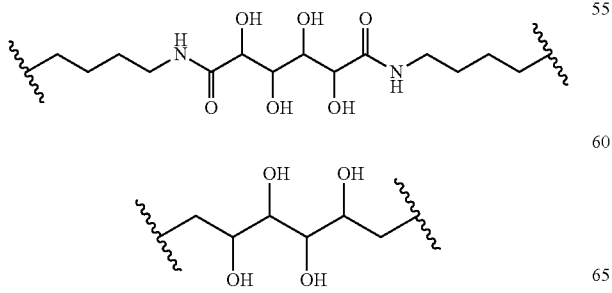

-continued

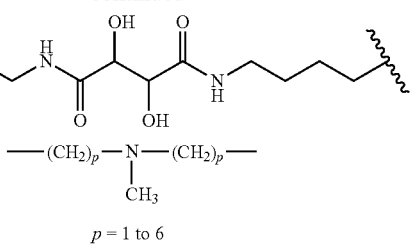

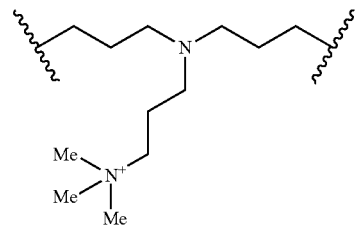

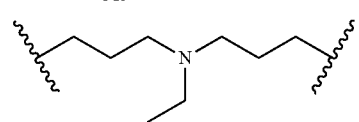

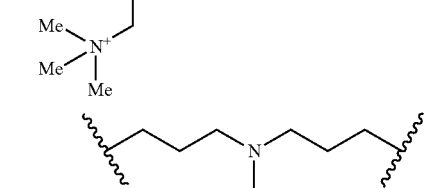

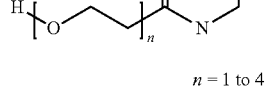

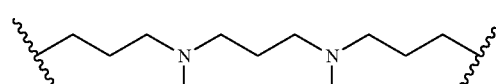

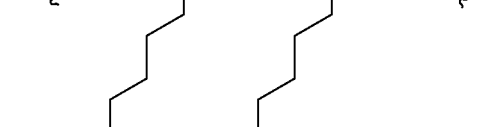

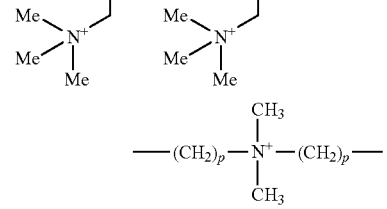

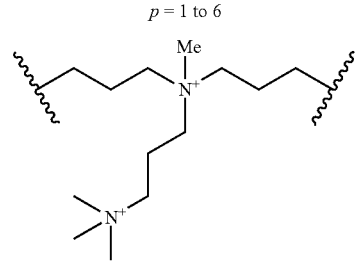

49
-continued

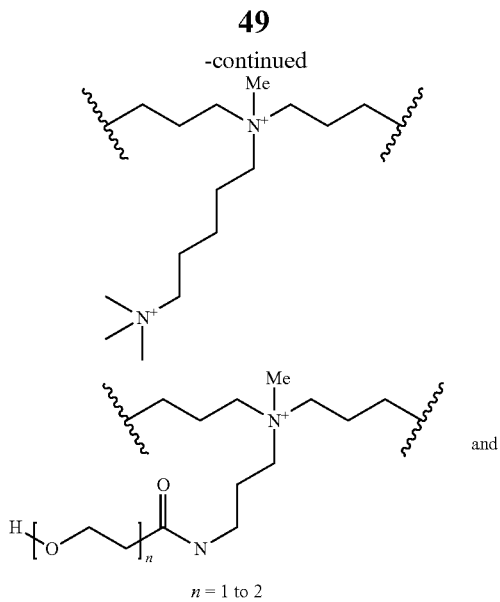

n = 1 to 2

50
-continued

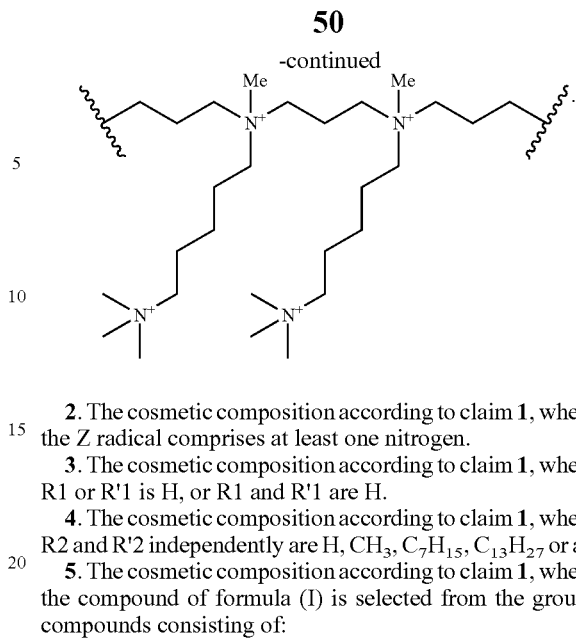

2. The cosmetic composition according to claim 1, wherein the Z radical comprises at least one nitrogen.

3. The cosmetic composition according to claim 1, wherein R1 or R'1 is H, or R1 and R'1 are H.

4. The cosmetic composition according to claim 1, wherein R2 and R'2 independently are H, $CH_3$, $C_7H_{15}$, $C_{13}H_{27}$ or aryl.

5. The cosmetic composition according to claim 1, wherein the compound of formula (I) is selected from the group of compounds consisting of:

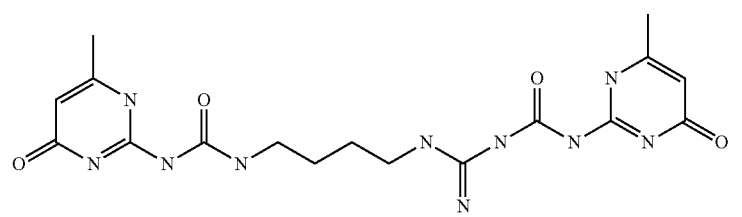

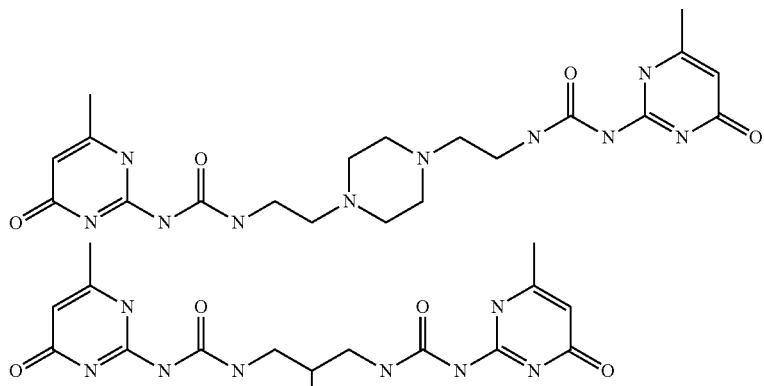

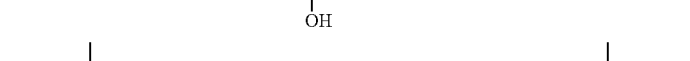

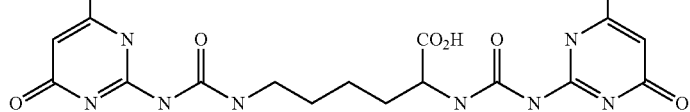

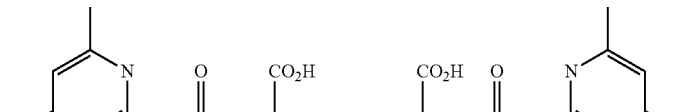

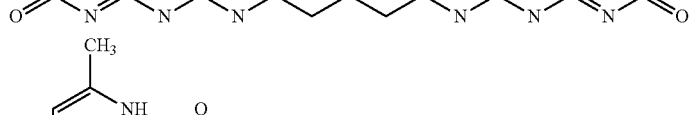

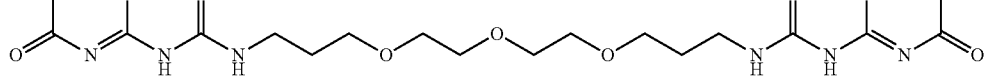

-continued
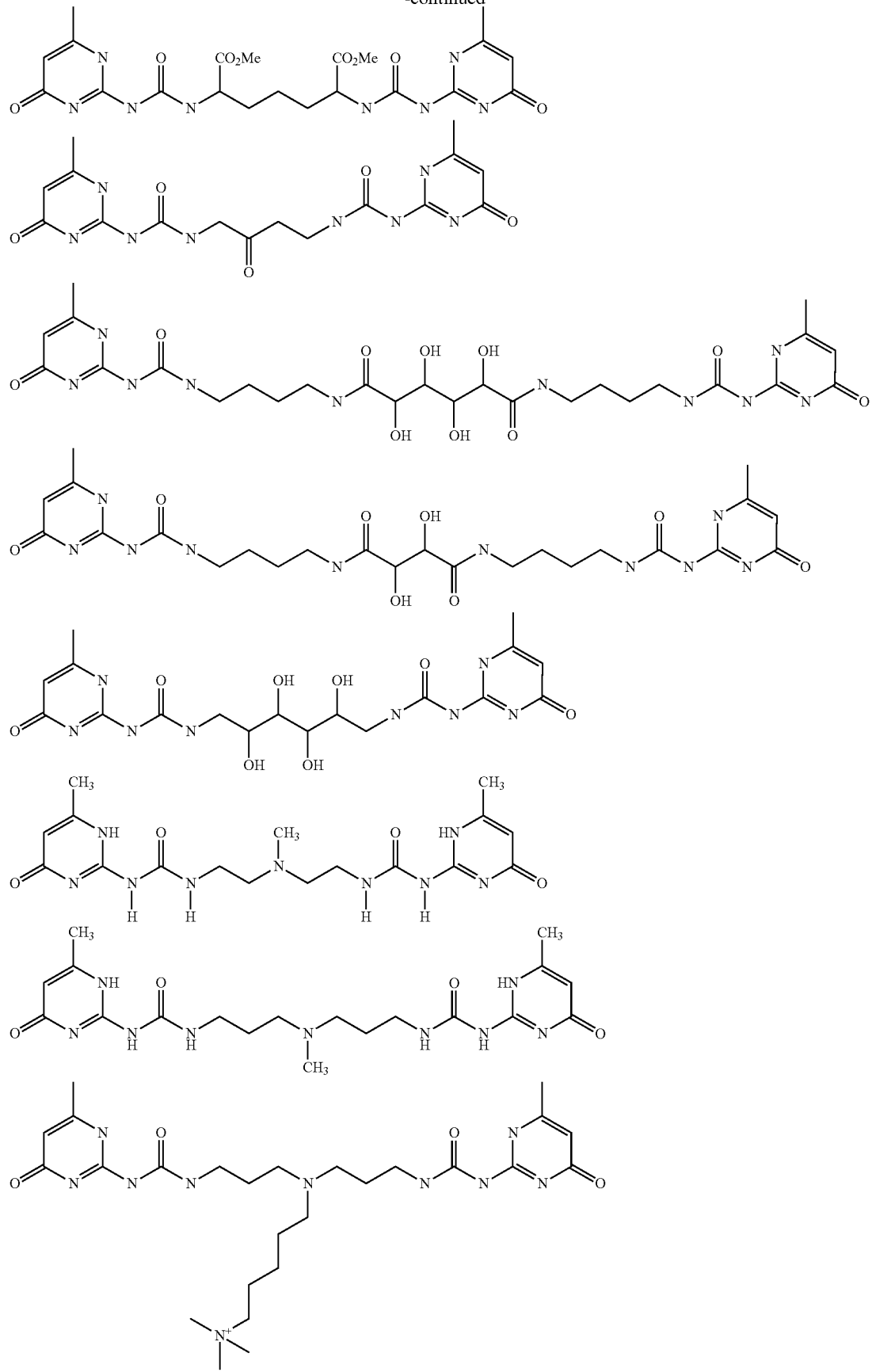

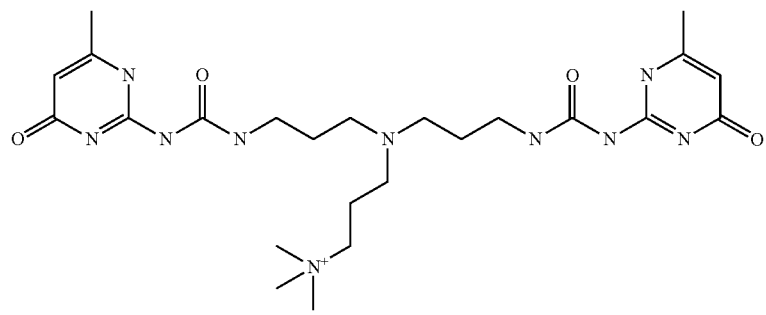
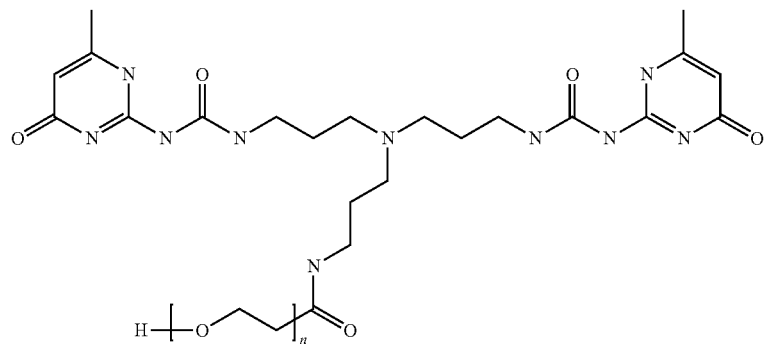
with *n* = 1 to 4
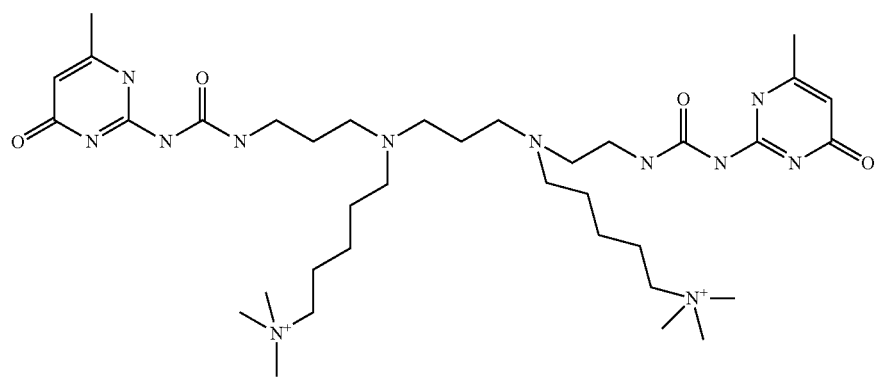
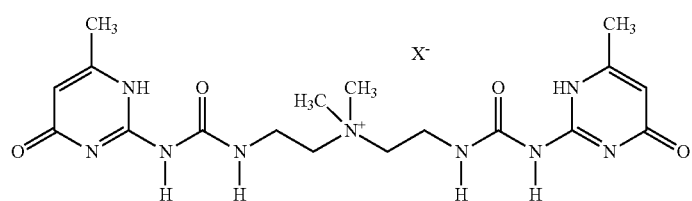
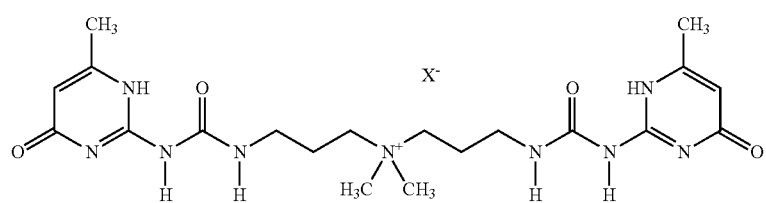

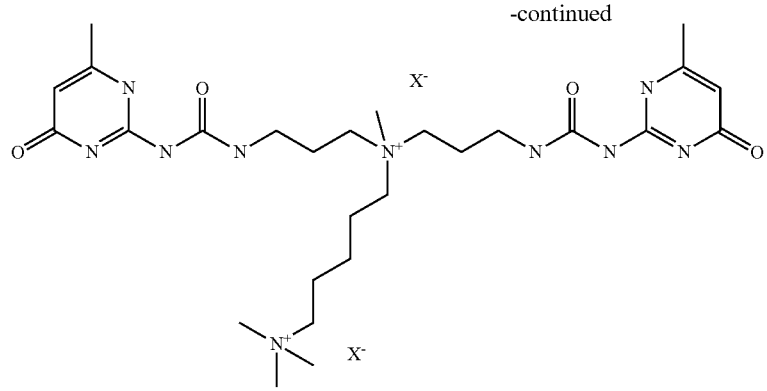
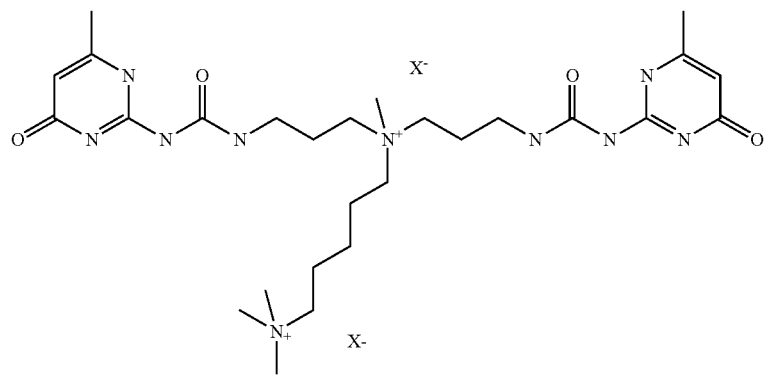
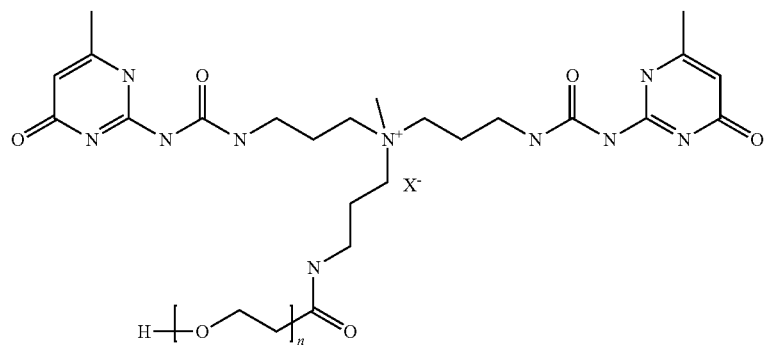
with n = 1 to 4
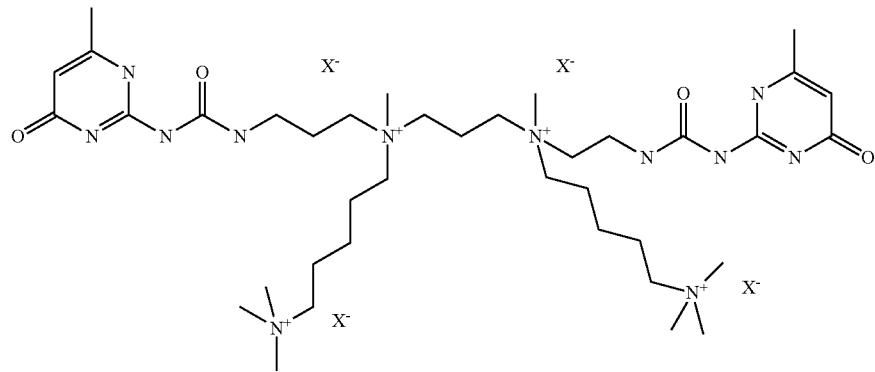
with X = Cl or Br -continued
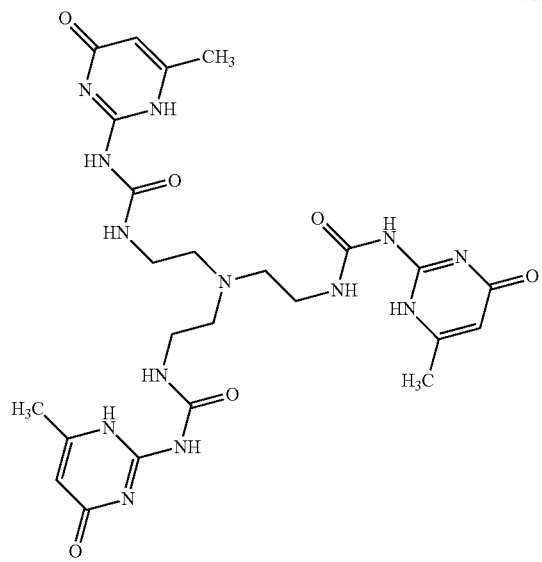
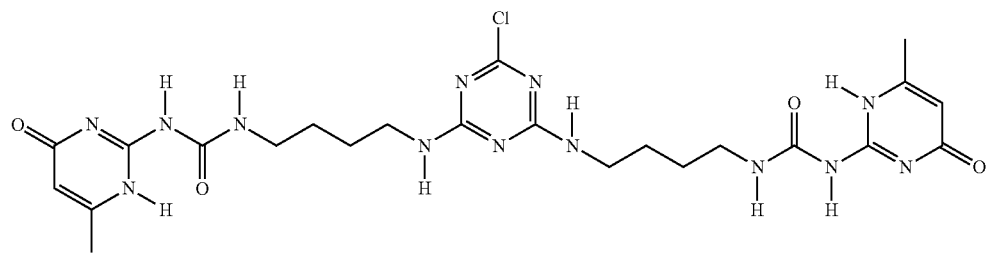
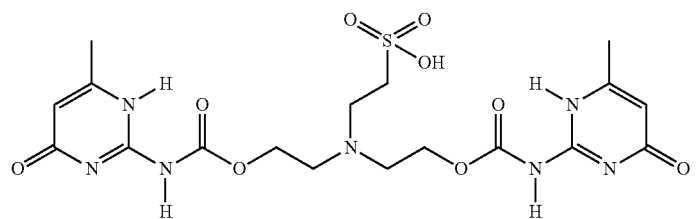
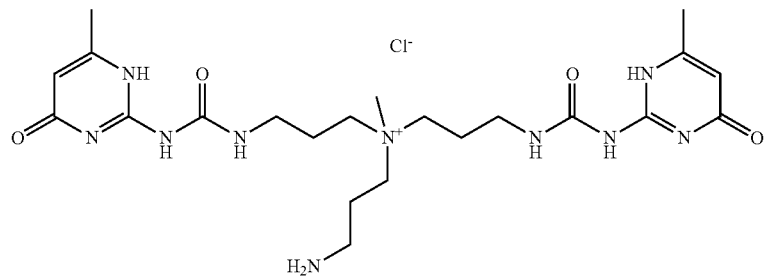
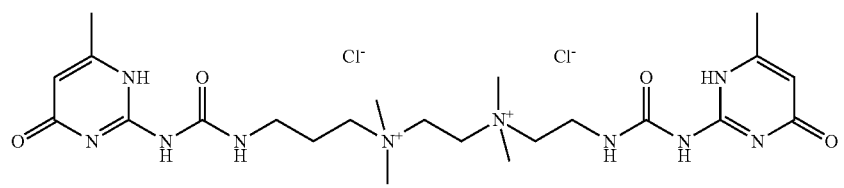

-continued

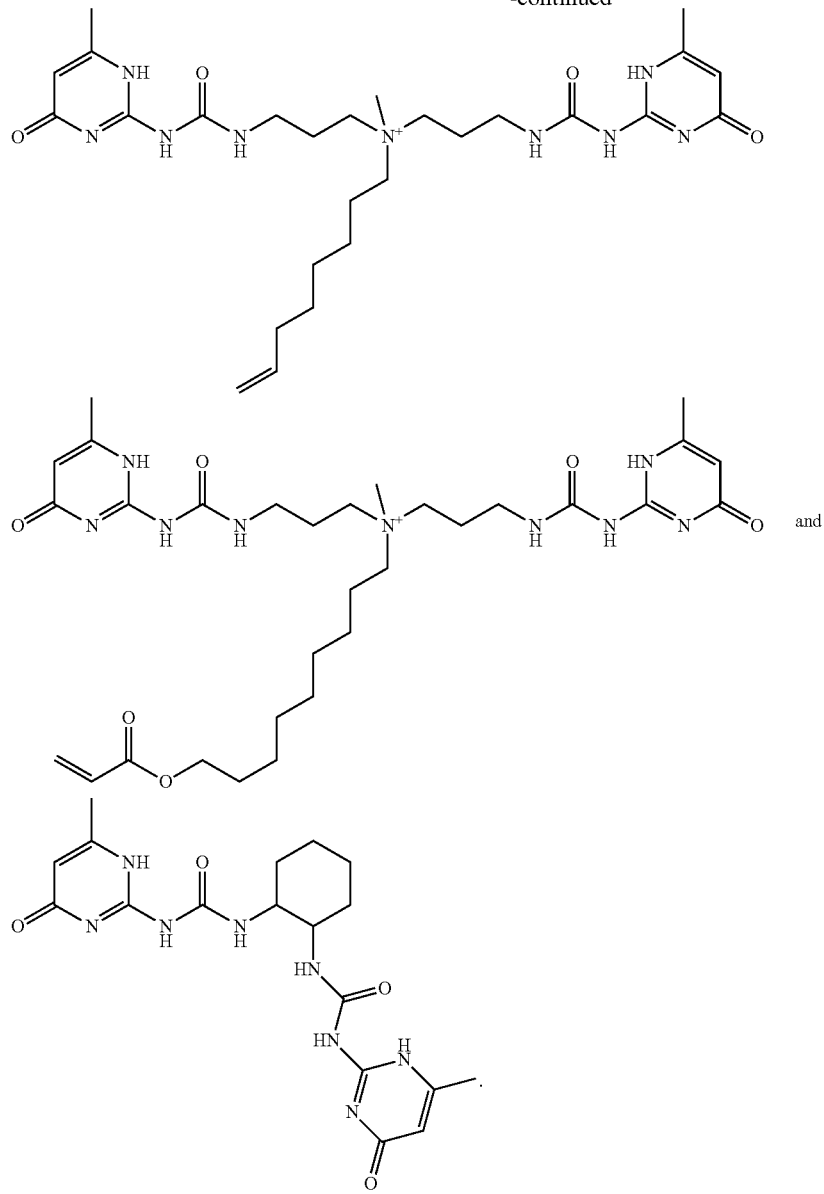

6. The cosmetic composition according to claim 1, wherein a content of the compound of formula (I) is from 0.001% to 15% by weight, relative to the total weight of the composition.

7. A cosmetic composition for hair care, cleansing of hair, styling of hair, hair form retention, hair shaping or hair dyeing comprising the composition according to claim 1.

8. A method for cosmetically treating keratin materials, which comprises applying a cosmetic composition as defined in claim 1 the keratin materials.

9. The method according to claim 8, wherein the keratin materials are hair.

10. The method according to claim 9, wherein the cosmetic treatment is for conditioning the hair, giving at least one of body and liveliness to the hair, or improving disentangling, smoothing, combability, repair and manageability of the hair.

11. The method according to claim 9, wherein the treatment is for at least one of repairing and protecting damaged or weakened hair.

12. A compound of formula (I):

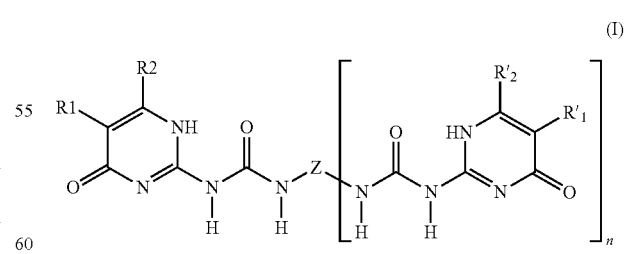

wherein:
n is 1;
R1, R'1, R2 and R'2, which may be identical or different within one and the same formula, are H, —OH, —NRR' with R and R', which may be identical or different, being H or a linear or branched C1-C12 alkyl radical; or a linear, branched and/or cyclic, saturated or unsaturated, optionally aromatic, C1-C18 carbon-based group which can contain one or more heteroatoms selected from the group consisting of O, S and N;
Z is a divalent radical selected from the group of radicals consisting of:
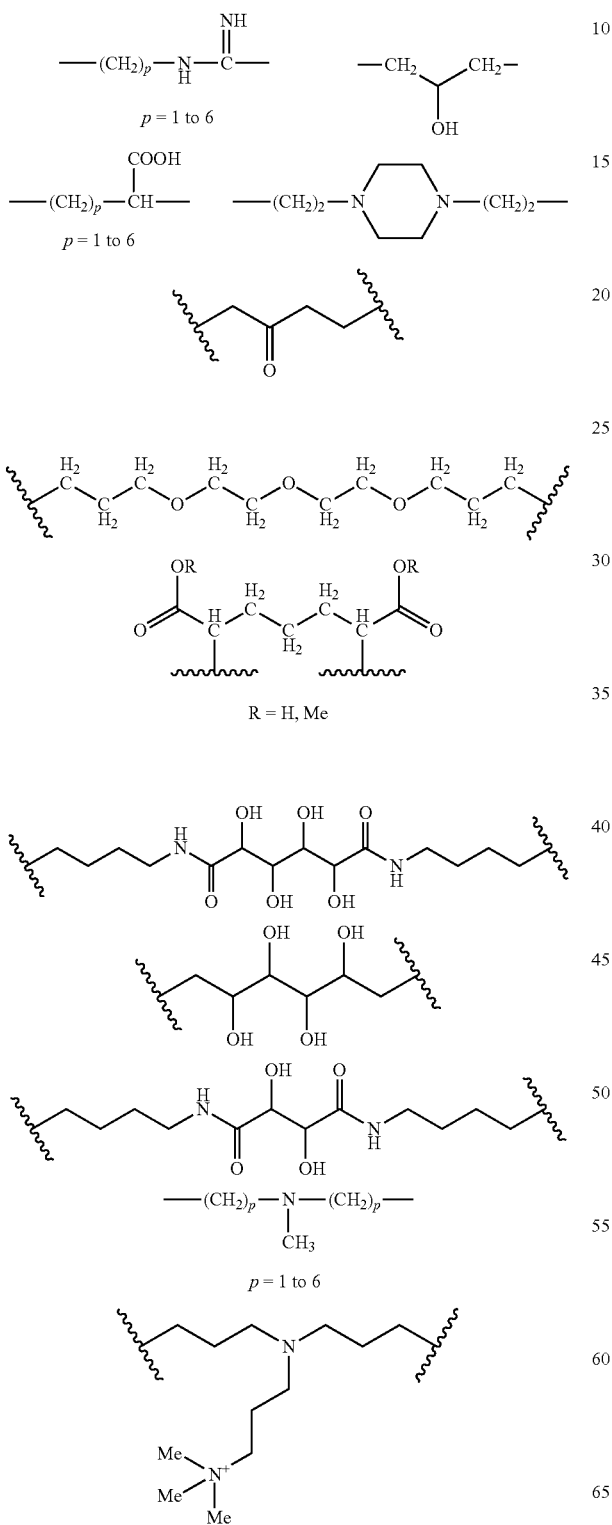
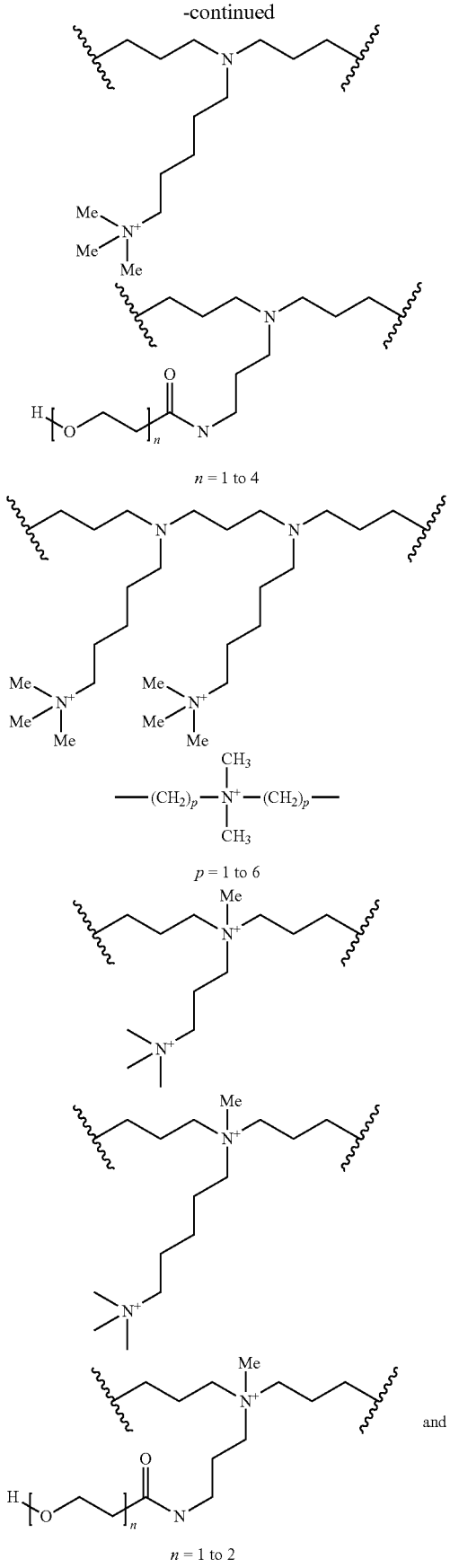

-continued

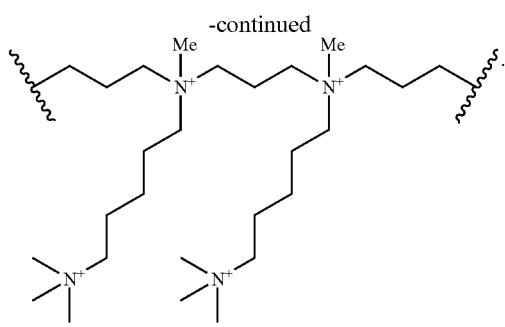

13. The cosmetic composition according to claim 1, wherein each of R2 and R'2 is H or CH3.

14. The cosmetic composition according to claim 1, wherein Z is

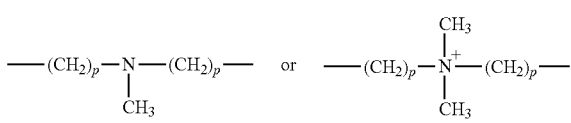

and p is 1 to 6.

15. The cosmetic composition according to claim 14, wherein p is 2 or 3.

16. The cosmetic composition according to claim 1, wherein at least one of R1 and R'1 is H, and Z is

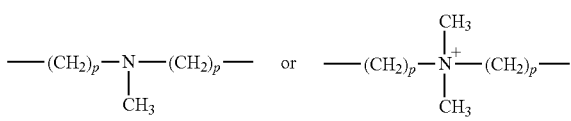

and p is 1 to 6.

17. The cosmetic composition according to claim 1, wherein compound (I) is selected from the group consisting of

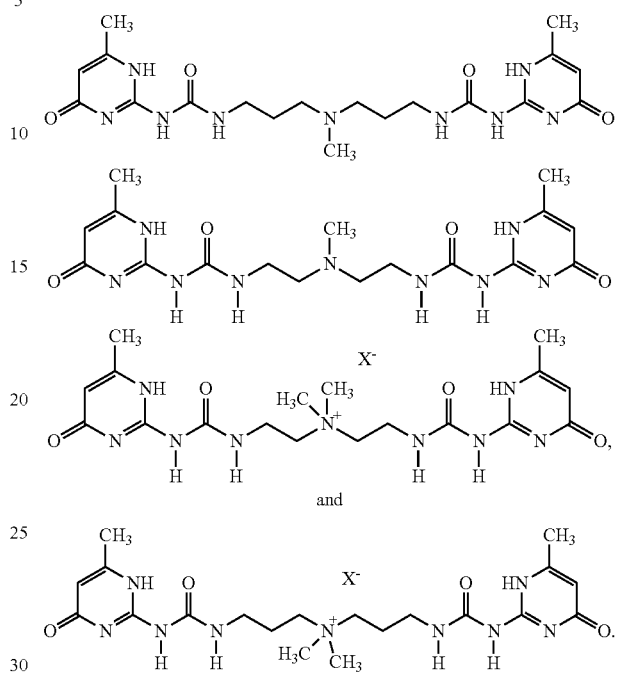

18. The compound according to claim 12, wherein the Z radical comprises at least one nitrogen.

19. The compound according to claim 12, wherein R1 or R'1 is H, or R1 and R'1 are H.

20. The compound according to claim 12, wherein R2 and R'2 independently are H, CH3, C7H15, C13H27 or aryl.

21. The compound according to claim 12, wherein the compound of formula (I) is selected from the group of compounds consisting of:

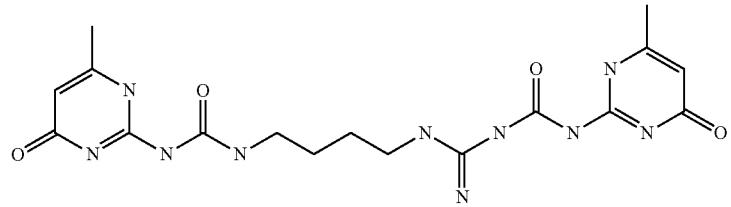

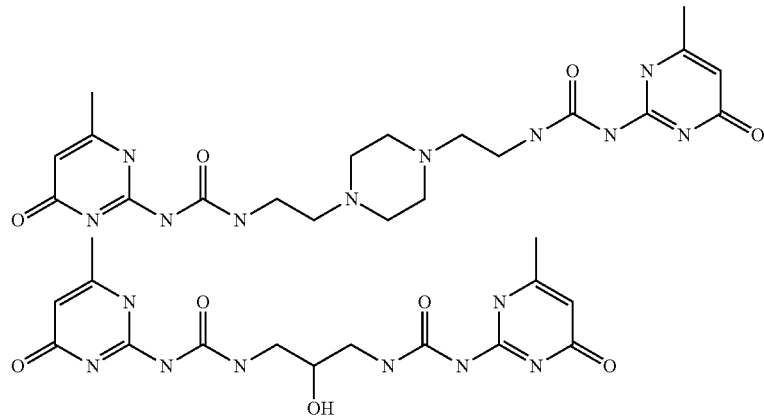

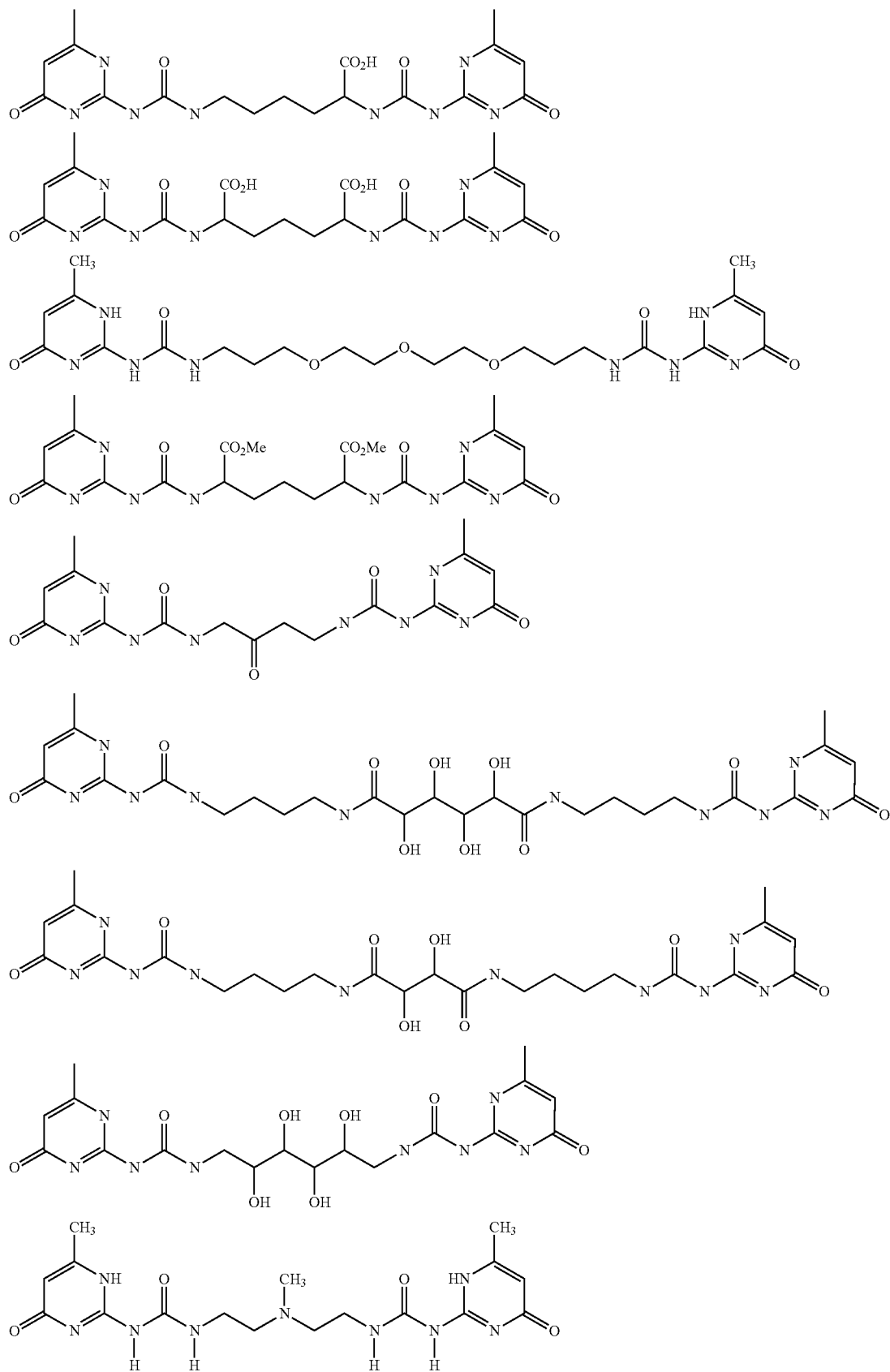

-continued
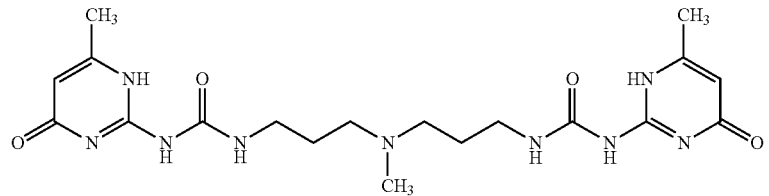
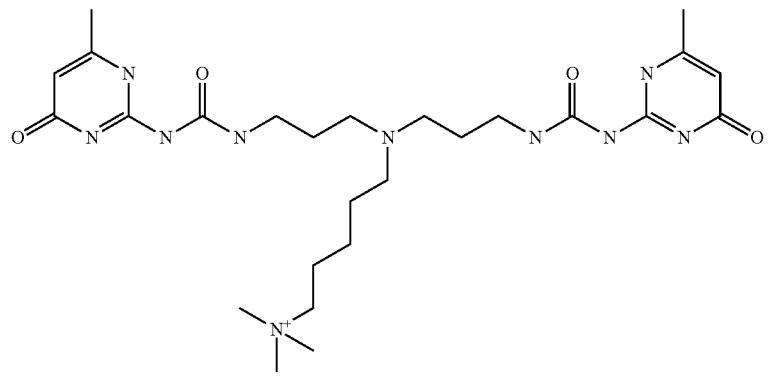
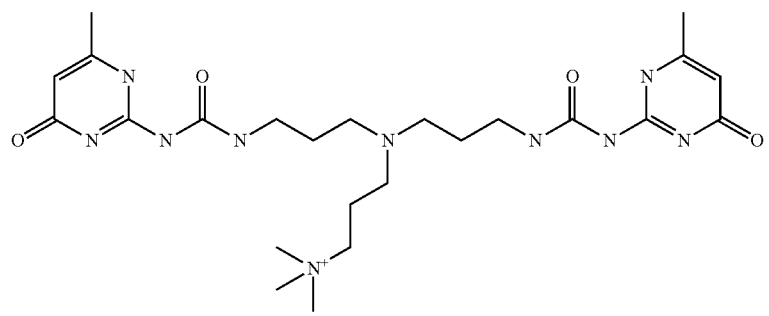
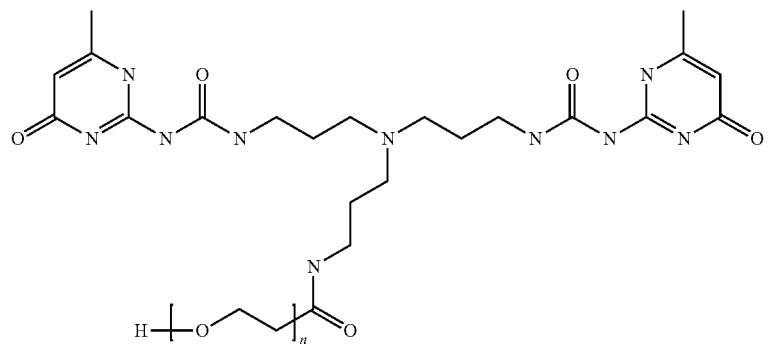
with n = 1 to 4
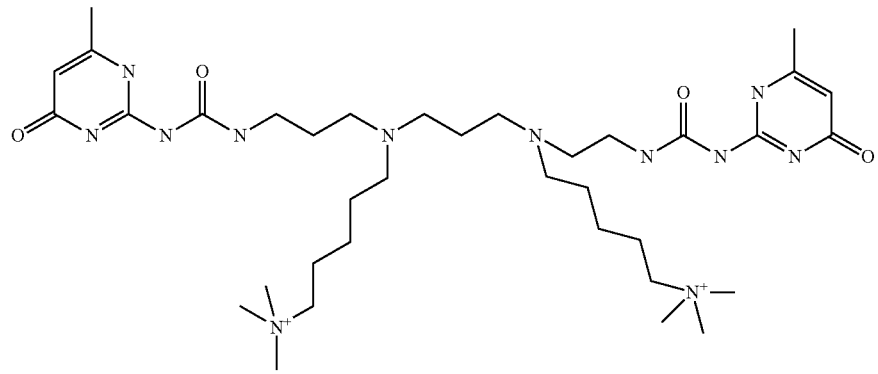

-continued
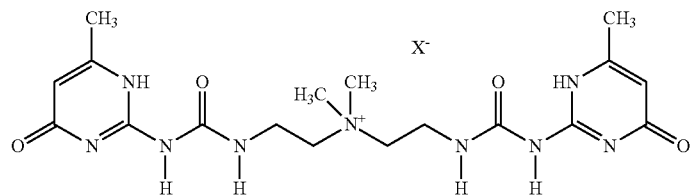
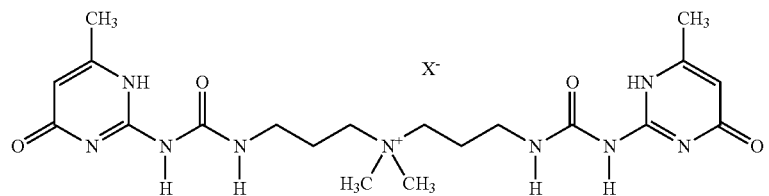
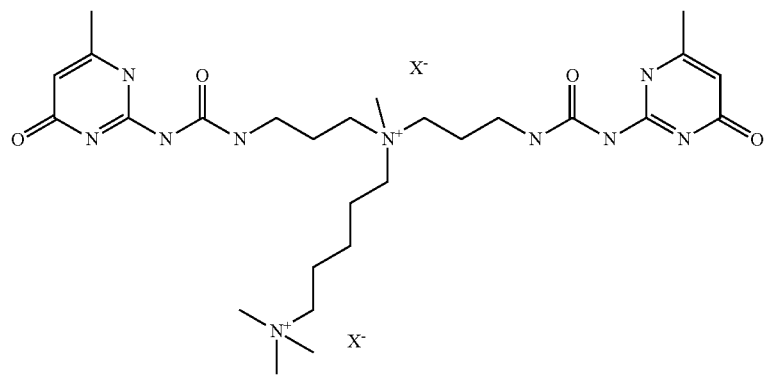
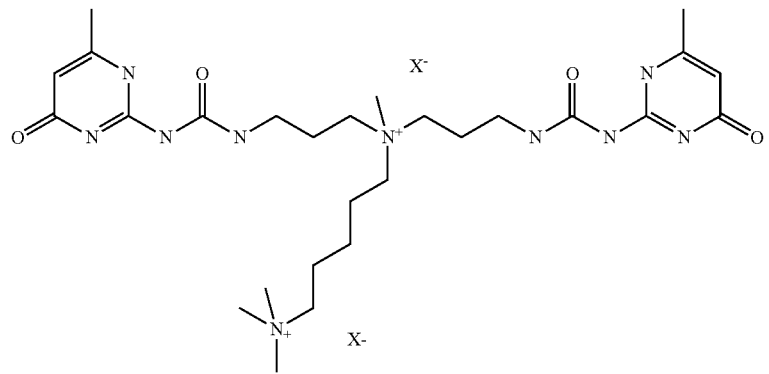
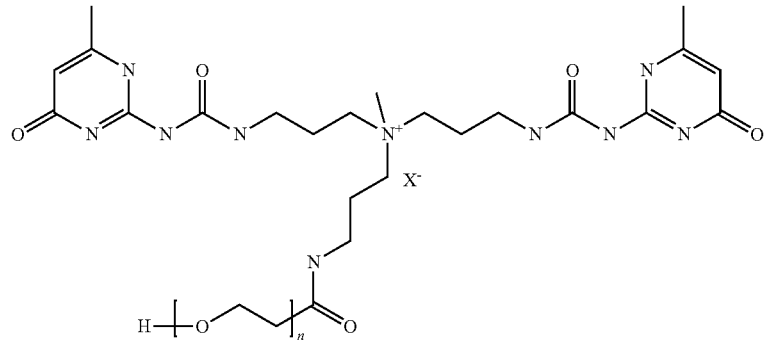
with $n = 1$ to $4$

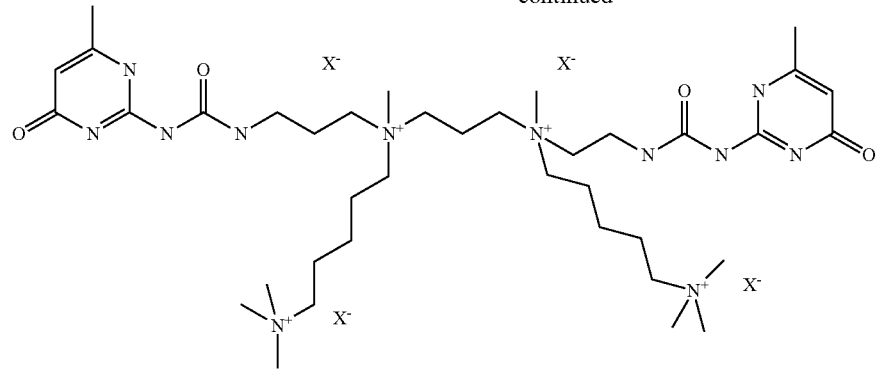
with X = Cl or Br
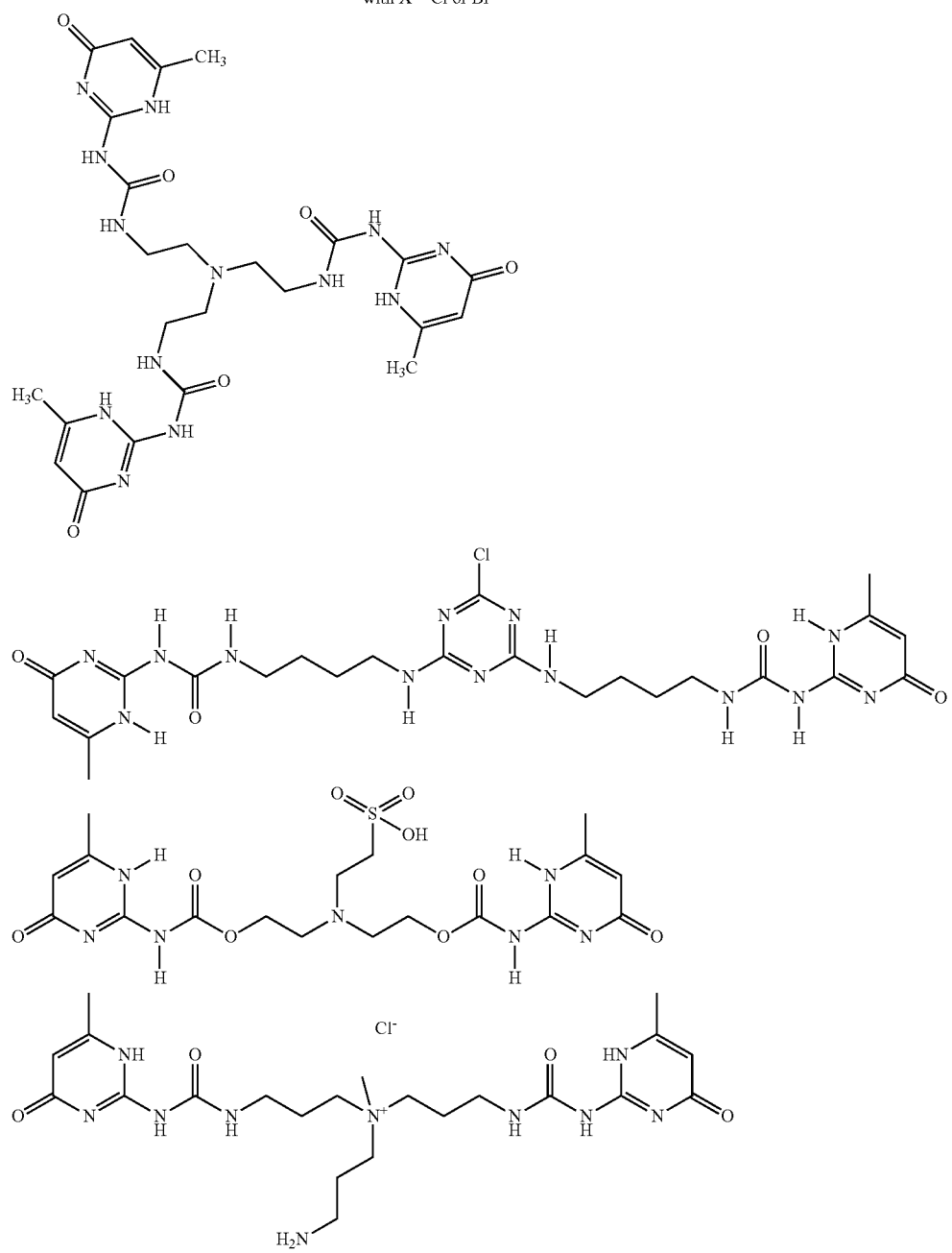

-continued
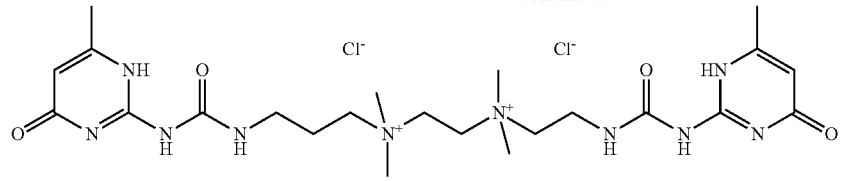
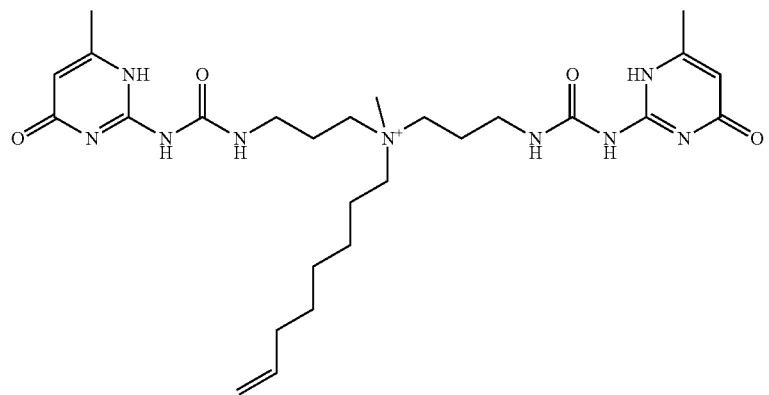
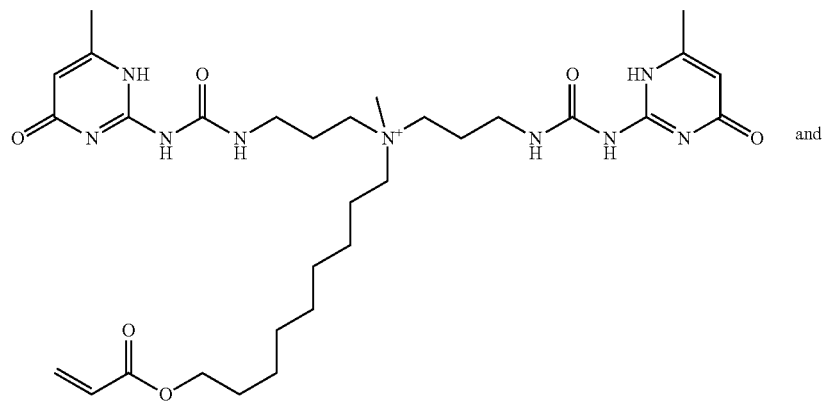 and
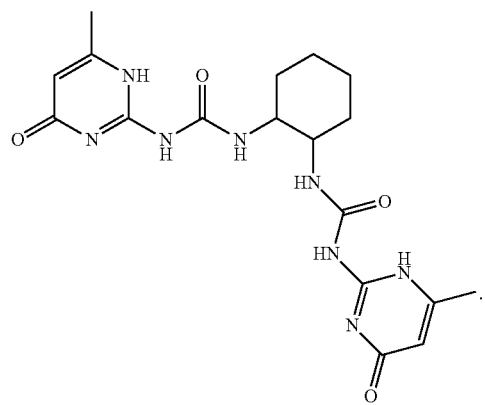 [SMILES: Cc1cc(=O)nc(NC(=O)NC2CCCCC2NC(=O)Nc2nc(=O)cc(C)[nH]2)[nH]1].

22. A cosmetic composition for hair care, cleansing of hair, styling of hair, hair form retention, hair shaping or hair dyeing comprising the compound according to claim 12.

23. A method for cosmetically treating keratin materials, which comprises applying a compound according to claim 12 to the keratin materials.

24. The method according to claim 23, wherein the keratin materials are hair.

25. The method according to claim 24, wherein the cosmetic treatment is for conditioning the hair, giving at least one of body and liveliness to the hair, or improving disentangling, smoothing, combability, repair and manageability of the hair.

26. The method according to claim 24, wherein the treatment is for at least one of repairing and protecting damaged or weakened hair.

27. The compound according to claim 12, wherein each of R2 and R'2 is H or CH3.

28. The compound according to claim 12, wherein Z is

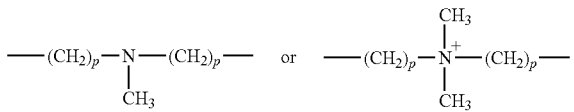

and p is 1 to 6.

29. The compound according to claim 12, wherein p is 2 or 3.

30. The compound according to claim 12, wherein at least one of R1 and R'1 is H, and Z is

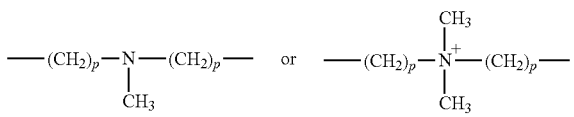

and p is 1 to 6.

31. The compound according to claim 12, wherein compound (I) is selected from the group consisting of

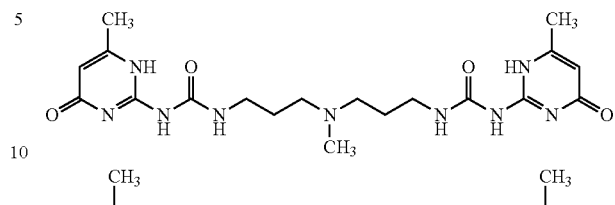

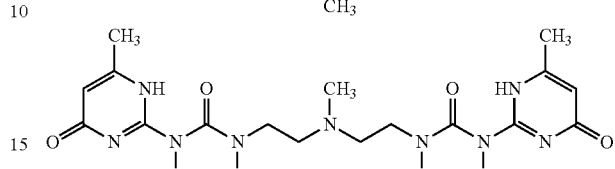

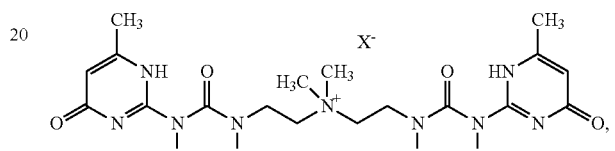

and

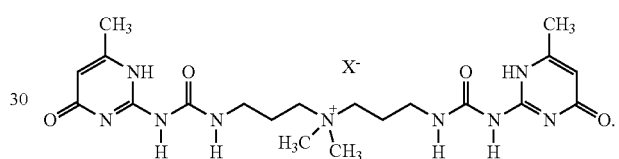

* * * * *